(12) United States Patent
Hatakeyama et al.

(10) Patent No.: US 6,743,564 B2
(45) Date of Patent: Jun. 1, 2004

(54) AMINE COMPOUNDS, RESIST COMPOSITIONS AND PATTERNING PROCESS

(75) Inventors: Jun Hatakeyama, Nakakubiki-gun (JP); Tomohiro Kobayashi, Nakakubiki-gun (JP); Takeru Watanabe, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 214 days.

(21) Appl. No.: 10/003,288

(22) Filed: Dec. 6, 2001

(65) Prior Publication Data

US 2002/0115018 A1 Aug. 22, 2002

(30) Foreign Application Priority Data

Dec. 7, 2000 (JP) ........................................ 2000-373316

(51) Int. Cl.$^7$ ........................... G03C 1/73; G03F 7/038; G03F 7/039; C07C 255/01
(52) U.S. Cl. .................... 430/270.1; 430/325; 430/326; 430/330; 430/327; 430/328; 430/296; 430/905; 430/914; 558/452; 544/106; 544/98; 544/56; 546/184; 546/330; 546/246; 548/215; 548/566; 548/579; 548/950; 548/954; 548/967; 548/969; 549/347; 549/352; 549/353; 549/494
(58) Field of Search ............................. 430/270.1, 296, 430/326, 330, 905, 914, 325, 327, 328; 544/106, 98, 56; 546/246, 184, 330; 548/566, 215, 579, 950, 954, 967, 969; 549/494, 347, 352, 353; 558/452

(56) References Cited

U.S. PATENT DOCUMENTS

| | | | |
|---|---|---|---|
| 3,457,349 A | * | 7/1969 | Jelinek ........................ 514/183 |
| 4,491,628 A | | 1/1985 | Ito et al. |
| 5,310,619 A | | 5/1994 | Crivello et al. |
| 5,580,695 A | | 12/1996 | Murata et al. |
| 5,609,989 A | | 3/1997 | Bantu et al. |
| 2001/0033993 A1 | * | 10/2001 | Kanna et al. ............. 430/285.1 |
| 2002/0102405 A1 | * | 8/2002 | Chapman et al. ........ 428/411.1 |

FOREIGN PATENT DOCUMENTS

| | | |
|---|---|---|
| JP | 63027829 A | 2/1988 |
| JP | 63149640 A | 6/1988 |
| JP | 90027660 B | 6/1990 |
| JP | 5113666 A | 5/1993 |
| JP | 5232706 A | 9/1993 |
| JP | 5249683 A | 9/1993 |
| WO | WO 9837458 A1 | 8/1998 |

OTHER PUBLICATIONS

Chem. Abstract 1987 : 156487—abstract for EP 209763 A1 ( Banasiak et al.), 1987.*
Chem. Abstract 1980 : 426787—abstract for "Some ester derivatives of 2–methylalanine as intermediates in peptide synthesis" (Stewart) Australian Journal of Chemistry, 33 (1), p. 121–9, 1980.*
Hinsberg et al., "Fundamental Studies of Airborne Chemical Contamination of Chemically Amplified Resists," *Journal of Photopolymer Science and Technology*, vol. 6, No. 4 (1993) pp 535–546.
Kumada, et al., "Study on Over–Top Coating of Positive Chemical Amplification Resists for KrF Excimer Laser Lithography," *Journal of Photopolymer Science and Technology*, vol. 6, No. 4 (1993) pp 571–574.
Hatakeyama, et al., "Investigation of Discrimination Enhancement with New Modeling for Poly–hydroxystyrene Positive Resists," *Journal of Photopolymer Science and Technology*, vol. 13, No. 4 (2000) pp 519–524.

* cited by examiner

Primary Examiner—Mark F. Huff
Assistant Examiner—Sin J. Lee
(74) Attorney, Agent, or Firm—Millen, White, Zelano & Branigan, P.C.

(57) ABSTRACT

Amine compounds having a cyano group are useful in resist compositions for preventing a resist film from thinning and also for enhancing the resolution and focus margin of resist.

27 Claims, No Drawings

AMINE COMPOUNDS, RESIST COMPOSITIONS AND PATTERNING PROCESS

BACKGROUND OF THE INVENTION

1. Field of the Invention

This invention relates to novel amine compounds useful as a basic component in resist compositions, novel resist compositions suitable for microfabrication comprising the amine compounds, and a patterning processing using the same.

2. Prior Art

While a number of efforts are currently made to achieve a finer pattern rule in the drive for higher integration and operating speeds in LSI devices, deep-ultraviolet lithography is thought to hold particular promise as the next generation in microfabrication technology. Deep-UV lithography is capable of pattern generation to dimensions of 0.2 μm or less and, when a resist material having low light absorption is used, can form patterns with sidewalls that are nearly vertical to the substrate. One technology that has attracted a good deal of attention recently utilizes a high-intensity KrF excimer laser as the deep-UV light source. Resist materials with low light absorption and high sensitivity are needed to successfully apply this technology to large-volume production.

In light of this, acid-catalyzed chemically amplified positive resist materials were recently developed as disclosed in JP-B 2-27660, JP-A 63-27829, U.S. Pat. Nos. 4,491,628 and 5,310,619. Because of their excellent properties including sensitivity, resolution and dry-etching resistance, they are especially promising as resist materials for deep-UV lithography.

Chemically amplified resist materials, however, suffer from a post-exposure delay (PED) problem and a footing phenomenon. The PED problem is that in lithographic process, line patterns would have a T-top profile, that is, patterns become thick at the top if the leave-to-stand or delay time from exposure to post-exposure baking (PEB) is extended. The footing is a phenomenon that a pattern on a basic substrate, especially silicon nitride or titanium nitride substrate becomes widened in proximity to the substrate. It is believed that the T-top profile arises because the solubility of resist film is reduced in proximity to its surface whereas the footing arises because the solubility of resist film is reduced in proximity to the substrate. There also occurs a problem that dark reaction of eliminating acid labile groups proceeds in a PED duration from exposure to PEB, reducing the dimension of lines to be left. These problems are serious enough to prevent chemically amplified positive resist materials from practical application. Moreover, these problems not only complicate dimensional control in the lithographic process, but also adversely affect dimensional control in the processing of substrates using dry etching. In this regard, reference is made to W. Hinsberg et al., J. Photopolym. Sci. Technol., 6 (4), 535–546 (1993) and T. Kumada et al., J. Photopolym., Sci. Technol., 6 (4), 571–574 (1993).

It is understood that in chemically amplified positive resist materials, air-borne basic compounds Largely participate in the PED problem and basic compounds on the substrate surface largely participate in the footing phenomenon. Light exposure generates acid at: the resist surface which is deactivated through reaction with air-borne basic compounds. As the leave-to-stand or delay time from exposure to PEB is extended, the amount of thus deactivated acid increases to retard decomposition of acid labile groups. An insolubilized layer is then formed at the resist surface, resulting in a T-top profile.

It is well known that the addition of basic compounds to resist materials is effective to suppress the influence of air-borne basic compounds, thereby improving PED (see U.S. Pat. No. 5,609,989, WO 98/37458, JP-A 63-149640, JP-A 5-113666, JP-A 5-232706 and JP-A 5-249683). Among such basic compounds, nitrogenous compounds are well known, typically amine and amide compounds having a boiling point of 150° C. or higher. Illustrative examples include pyridine, polyvinyl pyridine, aniline, N-methylaniline, N,N-dimethylaniline, o-toluidine, m-toluidine, p-toluidine, 2,4-lutidine, quinoline, isoquinoline, formamide, N-methylformamide, N,N-dimethyl-formamide, acetamide, N-methylacetamide, N,N-dimethylacet-amide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and triazine compounds such as 2-(p-chlorophenyl)-4,6-trichloromethyl-s-triazine. Of these, pyrrolidone, N-methylpyrrolidone, o-aminobenzoic acid, m-aminobenzoic acid, p-aminobenzoic acid and 1,2-phenylenediamine are often used.

These nitrogenous compounds are weakly basic and can mitigate the T-top problem, but fail to control reaction or acid diffusion when highly reactive acid labile groups are used. The addition of weak bases allows the dark reaction during PED to proceed to unexposed areas, incurring sliming of line size and film thinning on line surface during PED. This problem may be overcome by adding strong bases. However, a higher basicity does not always bring good results. No satisfactory results are obtained when proton sponge, DBN, and DBU, which are known as a ultra-strong base and shown below, or quaternary amines such as tetramethylammonium hydroxide are added.

proton sponge

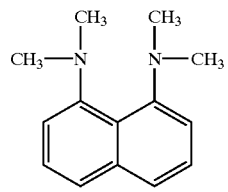

DBN: 1,5-diazabicyclo[4.3.0]-5-nonene

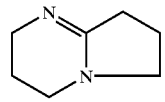

DBU: 1,8-diazabicyclo[5.4.0]-7-undecene

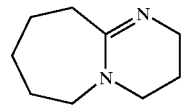

To enhance contrast to achieve a high resolution, it is advantageous to add a base which is more effective for complementing the acid generated. While the dissociation constant of an acid or base in water is accounted for in terms of pKa, the ability of a base to complement acid in the resist film is not directly related to the pKa of the base. This fact is discussed in Hatayama et al., J. of Photopolymer Sci. and Technology, Vol. 13, No. 4, pp. 519–524 (2000).

SUMMARY OF THE INVENTION

An object of the invention is to provide a novel amine compound which is effective for preventing a resist film from thinning and for expanding the focus margin while achieving an improved resolution. Another object is to provide a resist composition comprising the same and a patterning process using the composition.

The present inventor has found that amine compounds having a cyano group, specifically amine compounds having the following general formula (1), (2), (3) or (4), are fully effective for preventing a resist film from thinning and also effective for enhancing the resolution and focus margin of resist.

In a first aspect, the invention provides amine compounds of the following general formulae (1), (2), (3) and (4).

$$(R^2)_b N \text{—} (R^1 \text{—} CN)_a \quad (1)$$

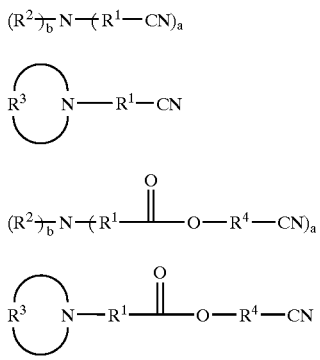

(2)

(3)

$$(R^2)_b N \text{—} (R^1 \text{—} \overset{O}{\underset{\|}{C}} \text{—} O \text{—} R^4 \text{—} CN)_a \quad$$

(4)

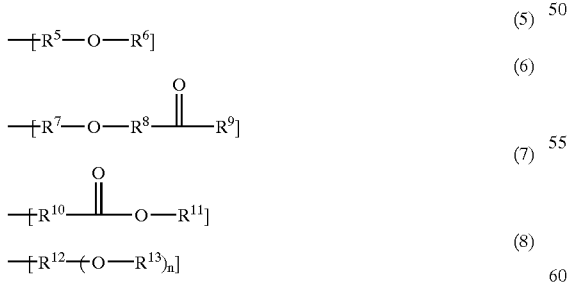

Herein $R^1$ is independently a straight or branched alkylene group of 1 to 4 carbon atoms; $R^2$ is independently hydrogen or a straight, branched or cyclic alkyl group of 1 to 20 carbon atoms which may contain a hydroxy group, ether group, carbonyl group, ester group, lactone ring, carbonate or cyano group; $R^3$ is a straight or branched alkylene group of 2 to 20 carbon atoms which may contain a hydroxy group, ether group, thioether group, carbonyl group, ester group, thioester group or carbonate; $R^4$ is independently a straight or branched alkylene group of 1 to 4 carbon atoms; "a" is an integer of 1 to 3, and a+b=3.

In a preferred embodiment, $R^2$ in formulae (1) and (3) has the following general formula (5), (6), (7) or (8).

$$\text{—}[R^5 \text{—} O \text{—} R^6] \quad (5)$$

$$\text{—}[R^7 \text{—} O \text{—} R^8 \text{—} \overset{O}{\underset{\|}{C}} \text{—} R^9] \quad (6)$$

$$\text{—}[R^{10} \text{—} \overset{O}{\underset{\|}{C}} \text{—} O \text{—} R^{11}] \quad (7)$$

$$\text{—}[R^{12} \text{—} (O \text{—} R^{13})_n] \quad (8)$$

Herein $R^5$, $R^7$ and $R^{10}$ each are a straight or branched alkylene group of 1 to 4 carbon atoms; $R^6$ and $R^9$ each are hydrogen or a straight, branched or cyclic alkyl group of 1 to 20 carbon atoms which may contain a hydroxy group, ether group, ester group, lactone ring or cyano group; $R^5$ and $R^6$, taken together, may form a ring with the oxygen atom; $R^8$ is a single bond or a straight or branched alkylene group of 1 to 4 carbon atoms; $R^{11}$ is a straight, branched or cyclic alkyl group of 1 to 20 carbon atoms which may contain a hydroxy group, ether group, ester group or lactone ring; $R^{12}$ is a (n+1)-valent straight or branched organic group of 1 to 4 carbon atoms; $R^{13}$ is independently a straight, branched or cyclic alkyl group of 1 to 10 carbon atoms which may contain an ether group, ester group, hydroxy group, lactone ring, cyano group or carbonyl group, $R^{12}$ and $R^{13}$ or two $R^{13}$ groups, taken together, may form a ring with the oxygen atom or the oxygen atom and a carbon atom in $R^{12}$; and n is equal to 2, 3 or 4.

In a second aspect, the invention provides a resist composition comprising a basic compound having a cyano group. In one preferred embodiment, the basic compound having a cyano group is at least one of amine compounds of the following general formulae (1), (2), (3) and (4).

$$(R^2)_b N \text{—} (R^1 \text{—} CN)_a \quad (1)$$

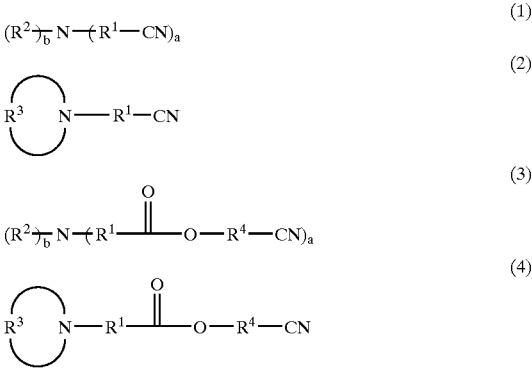

(2)

(3)

$$(R^2)_b N \text{—} (R^1 \text{—} \overset{O}{\underset{\|}{C}} \text{—} O \text{—} R^4 \text{—} CN)_a$$

(4)

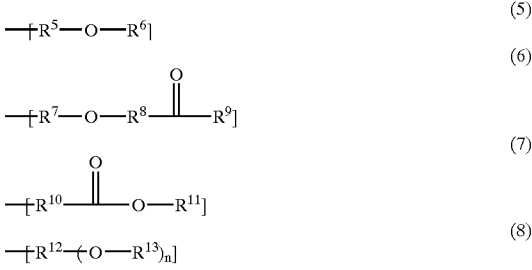

Herein $R^1$ is independently a straight or branched alkylene group of 1 to 4 carbon atoms; $R^2$ is independently hydrogen or a straight, branched or cyclic alkyl group of 1 to 20 carbon atoms which may contain a hydroxy group, ether group, carbonyl group, ester group, lactone ring, carbonate or cyano group; $R^3$ is a straight or branched alkylene group of 2 to 20 carbon atoms which may contain a hydroxy group, ether group, thioether group, carbonyl group, ester group, thioester group or carbonate; $R^4$ is independently a straight or branched alkylene group of 1 to 4 carbon atoms; "a" is an integer of 1 to 3, and a+b=3.

In a further preferred embodiment, $R^2$ in formulae (1) and (3) has the following general formula (5), (6), (7) or (8).

$$\text{—}[R^5 \text{—} O \text{—} R^6] \quad (5)$$

$$\text{—}[R^7 \text{—} O \text{—} R^8 \text{—} \overset{O}{\underset{\|}{C}} \text{—} R^9] \quad (6)$$

$$\text{—}[R^{10} \text{—} \overset{O}{\underset{\|}{C}} \text{—} O \text{—} R^{11}] \quad (7)$$

$$\text{—}[R^{12} \text{—} (O \text{—} R^{13})_n] \quad (8)$$

Herein $R^5$, $R^7$ and $R^{10}$ each are a straight or branched alkylene group of 1 to 4 carbon atoms; $R^6$ and $R^9$ each are hydrogen or a straight, branched or cyclic alkyl group of 1 to 20 carbon atoms which may contain a hydroxy group, ether group, ester group, lactone ring or cyano group; $R^5$ and $R^6$, taken together, may form a ring with the oxygen atom; $R^8$ is a single bond or a straight or branched alkylene group of 1 to 4 carbon atoms; $R^{11}$ is a straight, branched or cyclic alkyl group of 1 to 20 carbon atoms which may contain a hydroxy group, ether group, ester group or lactone ring; $R^{12}$ is a (n+1)-valent straight or branched organic group of 1 to 4 carbon atoms; $R^{13}$ is independently a straight, branched or cyclic alkyl group of 1 to 10 carbon atoms which may contain an ether group, ester group, hydroxy group, lactone ring, cyano group or carbonyl group, $R^{12}$ and $R^{13}$ or two $R^{13}$ groups, taken together, may form a ring with the oxygen atom or the oxygen atom and a carbon atom in $R^{12}$; and n is equal to 2, 3 or 4.

The resist composition is typically a positive resist composition comprising (A) the amine compound defined above, (B) an organic solvent, (C) a base resin having an acidic functional group protected with an acid labile group, which is normally alkali insoluble or substantially alkali insoluble, but becomes alkali soluble upon elimination of the acid labile group, and (D) a photoacid generator. The positive resist composition may further comprise (E) a dissolution inhibitor.

Alternatively, the resist composition is a negative resist composition comprising (A) the amine compound defined above, (B) an organic solvent, (C) a base resin which is normally alkali soluble, but becomes substantially alkali insoluble when crosslinked with a crosslinker, (D) a photo-acid generator, and (F) the crosslinker capable of crosslinking under the action of acid.

In a third aspect, the invention provides a process for forming a resist pattern comprising the steps of applying the resist composition defined above onto a substrate to form a coating; heat treating the coating and then exposing it to high-energy radiation having a wavelength of less than 300 nm or electron beams through a photo mask; and optionally heat treating the exposed coating and developing it with a developer.

DESCRIPTION OF THE PREFERRED EMBODIMENTS

Amine Compound

The amine compounds of the invention have the following general formulae (1), (2), (3) and (4).

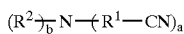

(1)

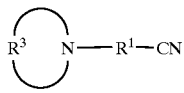

(2)

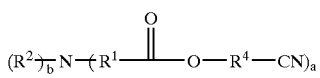

(3)

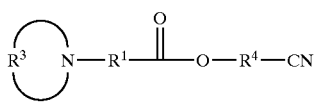

(4)

In formulae (1) to (4), $R^1$ which may be the same or different is a straight or branched alkylene group of 1 to 4 carbon atoms; $R^2$ which may be the same or different is hydrogen or a straight, branched or cyclic alkyl group of 1 to 20 carbon atoms which may contain a hydroxy group, ether group, carbonyl group, ester group, lactone ring, carbonate or cyano group; $R^3$ is a straight or branched alkylene group of 2 to 20 carbon atoms which may contain a hydroxy group, ether group, thioether group, carbonyl group, ester group, thioester group or carbonate; $R^4$ which may be the same or different is a straight or branched alkylene group of 1 to 4 carbon atoms; the subscript "a" is an integer of 1 to 3, and a+b=3.

Examples of the straight or branched alkylene group of 1 to 4 carbon atoms represented by $R^1$ and $R^4$ include methylene, ethylene, propylene, and butylene. $R^2$ is hydrogen or a straight, branched or cyclic alkyl group of 1 to 20 carbon atoms, especially 1 to 10 carbon atoms, such as hydrogen, methyl, ethyl, propyl, isopropyl, n-butyl, isobutyl, tert-butyl, pentyl, cyclopentyl, hexyl, cyclohexyl, octyl, decyl and dodecyl. These alkyl groups may contain a hydroxy group, ether group, carbonyl group, ester group, lactone ring, carbonate linkage or cyano group.

In one preferred embodiment, $R^2$ in formulae (1) and (3) has the following general formula (5), (6), (7) or (8).

(5)

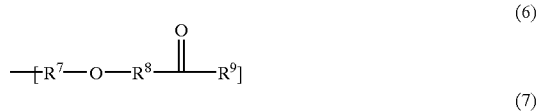

(6)

(7)

(8)

Herein $R^5$, $R^7$ and $R^{10}$ each are a straight or branched alkylene group of 1 to 4 carbon atoms. $R^6$ and $R^9$ each are hydrogen or a straight, branched or cyclic alkyl group of 1 to 20 carbon atoms, especially 1 to 10 carbon atoms, which may contain a hydroxy group, ether group, ester group, lactone ring or cyano group. $R^5$ and $R^6$, taken together, may form a ring with the oxygen atom, the ring having 3 to 20 carbon atoms, especially 4 to 12 carbon atoms. $R^8$ is a single bond or a straight or branched alkylene group of 1 to 4 carbon atoms. $R^{11}$ is a straight, branched or cyclic alkyl group of 1 to 20 carbon atoms which may contain a hydroxy group, ether group, ester group or lactone ring. $R^{12}$ is a (n+1)-valent straight or branched organic group of 1 to 4 carbon atoms, wherein n is equal to 2, 3 or 4.

Specifically, $R^{12}$ is a tri-, tetra- or penta-valent organic group. Illustrative are the hydrocarbon groups given below.

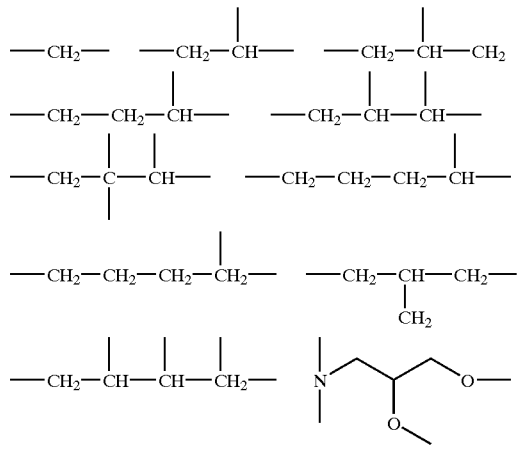

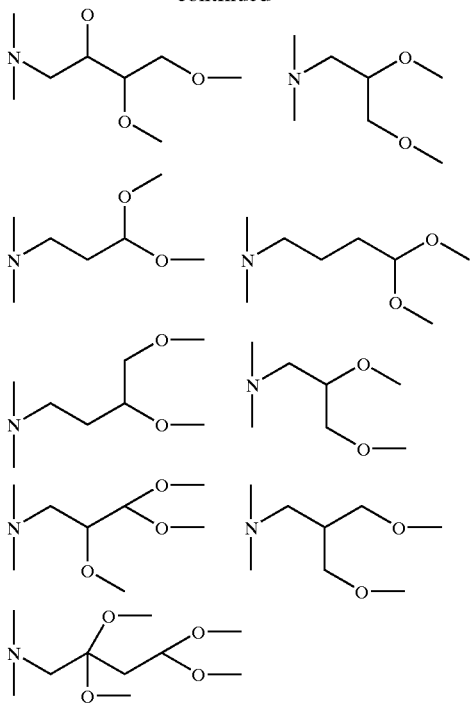

R[13] which may be the same or different is a straight, branched or cyclic alkyl group of 1 to 10 carbon atoms which may contain an ether group, ester group, hydroxy group, lactone ring, cyano group or carbonyl group. Such alkyl and alkoxy groups represented by R[13] are as illustrated above.

It is noted that R[12] and R[13], taken together, may bond with the oxygen atom to form a ring having 2 to 20 carbon atoms, especially 3 to 12 carbon atoms; and two R[13] groups, taken together, may bond with the oxygen atom or the oxygen atom and a carbon atom in R[12] to form a ring having 1 to 20 carbon atoms, especially 2 to 12 carbon atoms.

Illustrative examples of the groups of formulae (5), (6) (7) and (8) are given below by formulae (5)-1 to (5)-12, (6)-1 to (6)-12, (7)-1 to (7)-17, and (8)-1 to (8)-12, respectively.

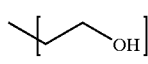 (5)-1

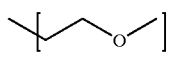 (5)-2

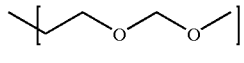 (5)-3

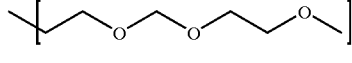 (5)-4

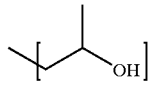 (5)-5

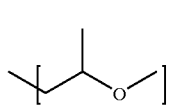 (5)-6

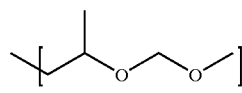 (5)-7

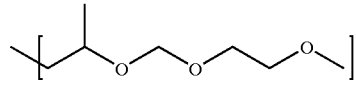 (5)-8

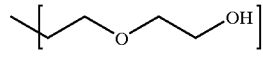 (5)-9

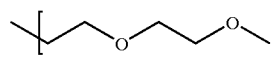 (5)-10

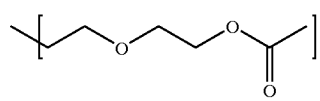 (5)-11

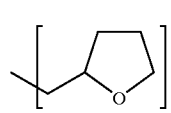 (5)-12

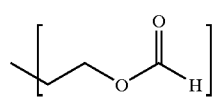 (6)-1

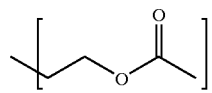 (6)-2

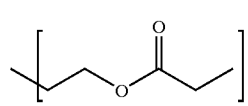 (6)-3

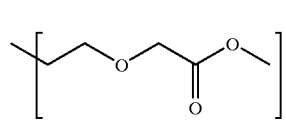 (6)-4

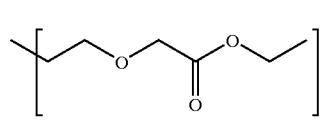 (6)-5

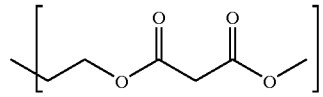 (6)-6

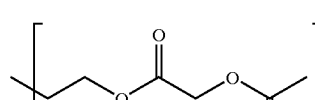 (6)-7

 (6)-8

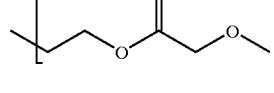 (6)-9

-continued

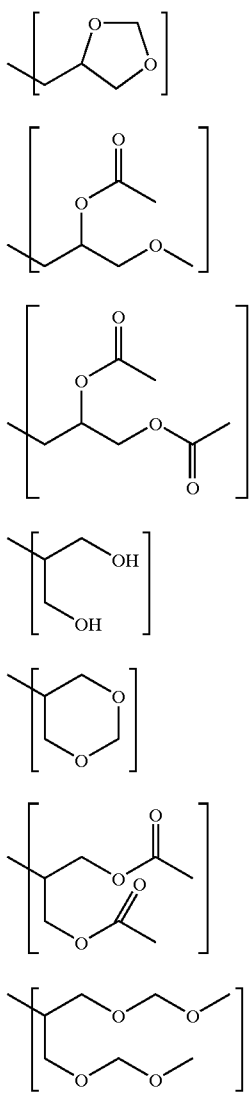
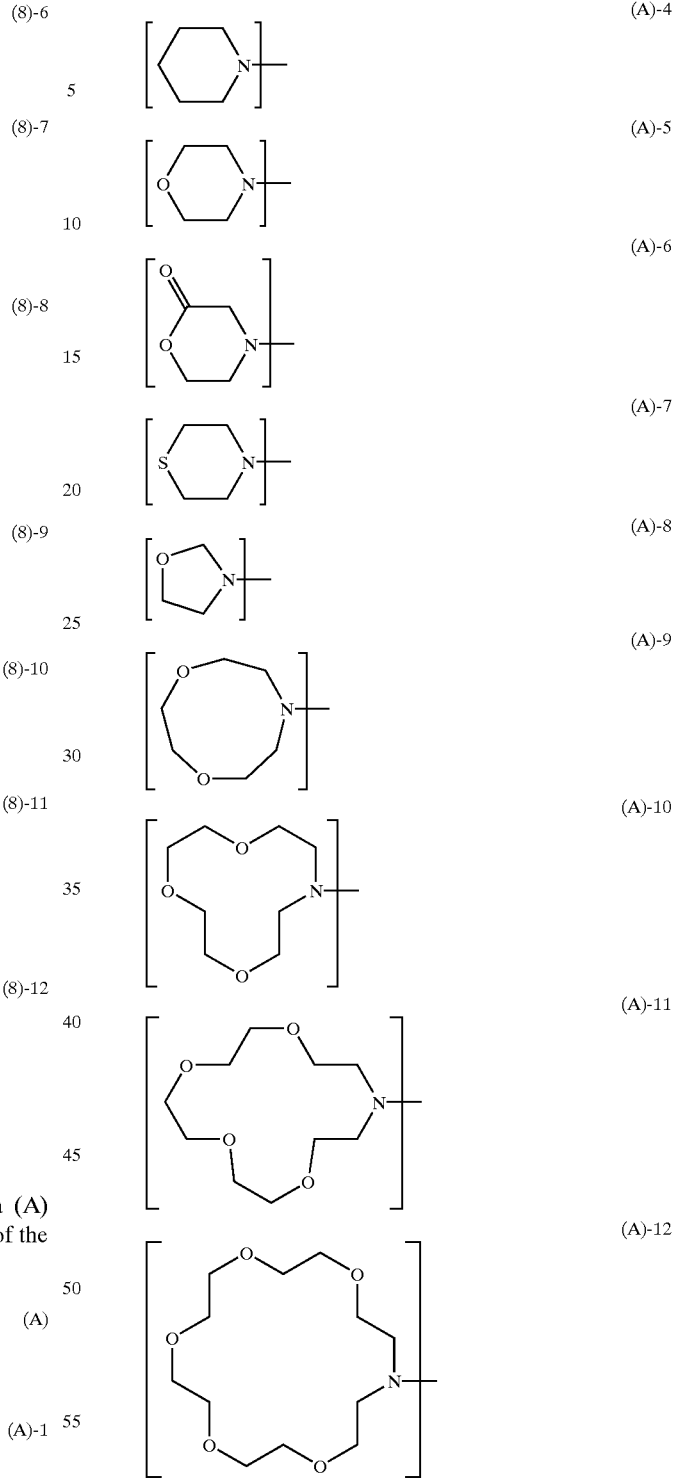

Illustrative of the group of the following formula (A) included in the above formulae (2) and (4) are groups of the following formulae (A)-1 to (A)-12.

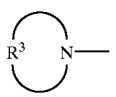
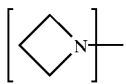
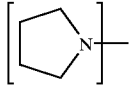

Illustrative examples of the amine compound of formula (1) include (3-diethylamino)propiononitrile,
N,N-bis(2-hydroxyethyl)-3-aminopropiononitrile,
N,N-bis(2-acetoxyethyl)-3-aminopropiononitrile,
N,N-bis(2-formyloxyethyl)-3-aminopropiononitrile,
N,N-bis(2-methoxyethyl)-3-aminopropiononitrile, N,N-bis[2-(methoxymethoxy)ethyl]-3-aminopropiononitrile,
methyl N-(2-cyanoethyl)-N-(2-methoxyethyl)-3-aminopripionate,
methyl N-(2-cyanoethyl)-N-(2-hydroxyethyl)-3-aminopropionate,
methyl N-(2-acetoxyethyl)-N-(2-cyanoethyl)-3-aminopropionate,
N-(2-cyanoethyl)-N-ethyl-3-aminopropionitrile,
N-(2-cyanoethyl)-N-(2-hydroxyethyl)-3-aminopropiononitrile,
N-(2-acetoxyethyl)-N-(2-cyanoethyl)-3-aminopropiononitrile,
N-(2-cyanoethyl)-N-(2-formyloxyethyl)-3-aminopropiononitrile,
N-(2-cyanoethyl)-N-(2-methoxyethyl)-3-aminopropiononitrile,
N-(2-cyanoethyl)-N-[2-(methoxymethoxy)ethyl]-3-aminopropiononitrile,
N-(2-cyanoethyl)-N-(3-hydroxy-1-propyl)-3-aminopropiononitrile,
N-(3-acetoxy-1-propyl)-N-(2-cyanoethyl)-3-aminopropiononitrile,
N-(2-cyanoethyl)-N-(3-formyloxy-1-propyl)-3-aminopropiononitrile,
N-(2-cyanoethyl)-N-tetrahydrofurfuryl-3-aminopropiononitrile,
N,N-bis(2-cyanoethyl)-3-aminopropiononitrile,
diethylaminoacetonitrile,
N,N-bis(2-hydroxyethyl)aminoacetonitrile,
N,N-bis(2-acetoxyethyl)aminoacetonitrile,
N,N-bis(2-formyloxyethyl)aminoacetonitrile,
N,N-bis(2-methoxyethyl)aminoacetonitrile,
N,N-bis[2-(methoxymethoxy)ethyl]aminoacetonitrile,
methyl N-cyanomethyl-N-(2-methoxyethyl)-3-aminopropionate,
methyl N-cyanomethyl-N-(2-hydroxyethyl)-3-aminopropionate,
methyl N-(2-acetoxyethyl)-N-cyanomethyl-3-aminopropionate,
methyl N-cyanomethyl-N-(2-formyloxyethyl) aminopropionate,
N-cyanomethyl-N-(2-hydroxyethyl)aminoacetonitrile,
N-(2-acetoxyethyl)-N-(cyanomethyl)aminoacetonitrile,
N-cyanomethyl-N-(2-formyloxyethyl)aminoacetonitrile,
N-cyanomethyl-N-(2-methoxyethyl)aminoacetonitrile,
N-cyanomethyl-N-[2-(methoxymethoxy)ethyl]aminoacetonitrile,
N-(cyanomethyl)-N-(3-hydroxy-1-propyl) aminoacetonitrile,
N-(3-acetoxy-1-propyl)-N-(cyanomethyl)aminoacetonitrile,
N-cyanomethyl-N-(3-formyloxy-1-propyl) aminoacetonitrile, and
N,N-bis(cyanomethyl)aminoacetonitrile.

Illustrative examples of the amine compound of formula (2) include 1-pyrrolidinepropiononitrile,
1-piperidinepropiononitrile,
4-morpholinepropiononitrile,
1-aziridinepropiononitrile,
1-azetidinepropiononitrile,
1-pyrrolidineacetonitrile,
1-piperidineacetonitrile, and
4-morpholineacetonitrile.

Illustrative examples of the amine compound of formula (3) include
cyanomethyl 3-diethylaminopropionate,
cyanomethyl N,N-bis(2-hydroxyethyl)-3-aminopropionate,
cyanomethyl N,N-bis(2-acetoxyethyl)-3-aminopropionate,
cyanomethyl N,N-bis(2-formyloxyethyl)-3-aminopropionate,
cyanomethyl N,N-bis(2-methoxyethyl)-3-aminopropionate,
cyanomethyl N,N-bis[2-(methoxymethoxy)ethyl]-3-aminopropionate,
2-cyanoethyl 3-diethylaminopropionate,
2-cyanoethyl N,N-bis(2-hydroxyethyl)-3-aminopropionate,
2-cyanoethyl N,N-bis(2-acetoxyethyl)-3-aminopropionate,
2-cyanoethyl N,N-bis(2-formyloxyethyl)-3-aminopropionate,
2-cyanoethyl N,N-bis(2-methoxyethyl)-3-aminopropionate,
2-cyanoethyl N,N-bis[2-(methoxymethoxy)ethyl]-3-aminopropionate,
cyanomethyl N,N-bis(2-cyanoethyl)-3-aminopropionate,
2-cyanoethyl N,N-bis(2-cyanoethyl)-3-aminopropionate,
cyanomethyl N,N-bis(cyanomethyl)-3-aminopropionate, and
2-cyanoethyl N,N-bis(cyanomethyl)-3-aminopropionate.

Illustrative examples of the amine compound of formula (4) include cyanomethyl 1-pyrrolidinepropionate,
cyanomethyl 1-piperidinepropionate,
cyanomethyl 4-morpholinepropionate,
2-cyanoethyl 1-pyrrolidinepropionate,
2-cyanoethyl 1-piperidinepropionate, and
2-cyanoethyl 4-morpholinepropionate.

The nitrile-containing amine compounds of formulae (1), (2), (3) and (4) according to the invention can be prepared by an appropriate method which is selected from several available methods depending on the structure of a particular compound although the method is not limited thereto. Several exemplary methods are described below in detail.

A first method is synthesis from a primary or secondary amine compound and an α,β-unsaturated nitrile compound (in the case of formulae (1) and (2)) or a nitrile-containing α,β-unsaturated ester compound (in the case of formulae (3) and (4)) utilizing Michael addition reaction on amine.

Exemplary α,β-unsaturated nitrile compounds are acrylonitrile and methacrylonitrile, though not limited thereto. Exemplary nitrile-containing α,β-unsaturated ester compounds are cyanomethyl acrylate, 2-cyanoethyl acrylate, and 2-cyanoethyl methacrylate, though not limited thereto.

An appropriate amount of the α,β-unsaturated nitrile compound or nitrile-containing α,β-unsaturated ester compound used per mol of the amine compound is 1.0 to 10 mol and especially 1.6 to 2.4 mol when the amine compound is a primary amine, and 0.5 to 5.0 mol and especially 0.8 to 1.2 mol when the amine compound is a secondary amine. The reaction is carried out in the presence or absence of solvent. Illustrative examples of the solvent include alcohols such as methanol, ethanol, isopropyl alcohol, t-butyl alcohol and ethylene glycol; hydrocarbon solvents such as hexane, heptane, benzene, toluene, and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacet-amide, dimethyl sulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. Any appropriate one or mixture may be selected from these solvents depending on the reaction conditions. The reaction temperature is selected in the range from 0° C. to the reflux temperature of the solvent, depending on the desired reaction rate. A catalyst may be added to the reaction system for accelerating the reaction rate. Exemplary catalysts include inorganic acids or salts thereof, such as hydrochloric acid, sulfuric acid and nitric acid, and organic acids or salts thereof, such as p-toluenesulfonic acid, formic acid, acetic acid, oxalic acid and trifluoroacetic acid. Also, a polymerization inhibitor such as hydroquinone, p-methoxyphenol, benzoquinone or phenylenediamine may be added to preclude the $\alpha,\beta$-unsaturated nitrile compound or nitrile-containing $\alpha,\beta$-unsaturated ester compound from polymerization. From the yield standpoint, the reaction is desirably continued to completion while monitoring the reaction by gas chromatography (GC) or thin layer chromatography (TLC), although the reaction time is usually about 2 to about 200 hours. The end nitrile-containing amine compound of formula (1), (2), (3) or (4) is obtained from the reaction mixture directly by vacuum concentration or by a conventional aqueous work-up step and subsequent vacuum concentration. If necessary, the end nitrile-containing amine compound thus obtained is purified by any conventional technique such as distillation, chromatography or recrystallization.

A second method is synthesis from a primary or secondary amine compound and a haloalkylnitrile compound (in the case of formulae (1) and (2)) or nitrile-containing halocarboxylic ester compound (in the case of formulae (3) and (4)) utilizing N-alkylation reaction on amine.

Illustrative, non-limiting examples of the haloalkyl-nitrile compound include bromoacetonitrile, chloroaceto-nitrile, 2-chloropropiononitrile, 3-chloropropiononitrile, 4-bromobutyronitrile and 5-bromopentanenitrile. Illustrative, non-limiting examples of the nitrile-containing halocarboxylic ester compound include cyanomethyl chloroacetate, 2-cyanoethyl chloroacetate, cyanomethyl 2-chloropropionate, 2-cyanoethyl 4-bromobutyrate and cyanomethyl 5-bromovalerate.

An appropriate amount of the haloalkylnitrile compound or nitrile-containing halocarboxylic ester compound used per mol of the amine compound is 1.0 to 20 mol and especially 1.6 to 4.8 mol when the amine compound is a primary amine, and 0.5 to 10 mol and especially 0.8 to 2.4 imol when the amine compound is a secondary amine. The reaction can be promoted by adding a basic compound. Illustrative, non-limiting examples of useful basic compounds include amines such as pyridine, triethylamine, diisopropylethylamine, N,N-dimethylaniline, 4-dimethylaminopyridine and 1,8-diaza-bicyclo[5.4.0]-7-undecene; and inorganic bases such as sodium hydroxide, potassium hydroxide, lithium hydroxide, potassium carbonate, sodium carbonate and sodium hydrogen carbonate. The basic compounds may be used alone or in admixture of any. An appropriate amount of the basic compound used is 0.1 to 10 mol and especially 0.8 to 2.0 mol per mol of the haloalkylnitrile compound or nitrile-containing halocarboxylic ester compound. A catalyst may also be added to accelerate the reaction, for example, sodium iodide or tetrabutylammonium iodide. An appropriate amount of the catalyst used is 0.001 to 0.5 mol and especially 0.005 to 0.1 mol per mol of the haloalkylnitrile compound or nitrile-containing halocarboxylic ester compound. The reaction is carried out in the presence or absence of solvent. Illustrative examples of the solvent include alcohols such as methanol, ethanol, isopropyl alcohol, t-butyl alcohol and ethylene glycol; hydrocarbon solvents such as hexane, heptane, benzene, toluene, and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacetamide, dimaethyl sulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethyl-amine; and water. Any appropriate one or mixture may be selected from these solvents depending on the reaction conditions. The reaction temperature is selected in the range from 0° C. to the reflux temperature of the solvent, depending on the desired reaction rate. From the yield standpoint, the reaction is desirably continued to completion while monitoring the reaction by gas chromatography (GC) or thin layer chromatography (TLC), although the reaction time is usually about 2 to about 200 hours. The end nitrile-containing amine compound of formula (1), (2), (3) or (4) is obtained from the reaction mixture by filtration or a conventional aqueous work-up step and subsequent vacuum concentration. If necessary, the end amine compound thus obtained is purified by any conventional technique such as distillation, chromatography or recrystallization.

Resist Composition

The resist compositions of the invention contain an amine compound containing a cyano group. This amine compound containing a cyano group is preferably of formulae (1), (2), (3) and (4) defined above.

The amount of the amine compound blended is preferably 0.001 to 2 parts and especially 0.01 to 1 part by weight per 100 parts by weight of the entire base resin, to be described later. Less than 0.001 part of the amine compound may fail to achieve the desired effects whereas more than 2 parts may result in a lower sensitivity.

The resist compositions containing the inventive amine compound may be either positive or negative working although they are preferably of the chemical amplification type.

One preferred embodiment of the invention is directed to a positive resist composition comprising (A) the amine compound defined above,
(B) an organic solvent,
(C) a base resin having an acidic functional group protected with an acid labile group, which is normally alkali insoluble or substantially alkali insoluble, but becomes alkali soluble upon elimination of the acid labile group,
(D) a photoacid generator, and optionally,
(E) a dissolution inhibitor.

Another preferred embodiment of the invention is directed to a negative resist composition comprising (A) the amine compound defined above,
(B) an organic solvent,
(C) a base resin which is normally alkali soluble, but becomes substantially alkali insoluble when crosslinked with a crosslinker,
(D) a photoacid generator, and
(F) the crosslinker capable of crosslinking under the action of acid.

Component (B) in the resist composition of the invention is an organic solvent, which may be any organic solvent in which the photoacid generator, base resin, dissolution inhibitor and other components are soluble. Usually 100 to 5,000 parts, and especially 200 to 3,000 parts by weight of the solvent is used per 100 parts by weight of the base resin. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in admixture of two or more. Of the above organic solvents, diethylene glycol dimethyl ether, 1-ethoxy-2-propanol and ethyl lactate in which the photoacid generator is most soluble, propylene glycol monomethyl ether acetate which is a safe solvent, and mixtures thereof are preferred.

Component (C) is a base resin. For resist compositions adapted for a KrF excimer laser, suitable base resins include polyhydroxystyrene (PHS) and copolymers of PHS with styrene, (meth)acrylates or maleimide-N-carboxylates. For resist compositions adapted for an ArF excimer laser, suitable base resins include (meth)acrylate polymers, alternating copolymers of norbornene and maleic anhydride, alternating copolymers of tetracyclododecene and maleic anhydride, norbornene polymers, and metathesis polymers by ring-opening polymerization. For resist compositions adapted for an $F_2$ excimer laser, suitable base resins include fluorinated ones of the polymers listed for the KrF and ArF applications and copolymers thereof with tetrafluoroethylene. These polymers are merely illustrative, and the base resin used herein is not limited thereto. For positive resist compositions, it is a common practice to reduce the dissolution rate of unexposed areas by partly substituting acid labile groups for hydrogen atoms on phenolic hydroxyl groups or carboxyl groups or hydroxyl groups on fluorinated alkyl alcohols.

In the base resin, the acid labile group is selected from a variety of such groups, and preferably from among groups of the following general formulae (9) and (10), tertiary alkyl groups with 4 to 40 carbon atoms of the following general formula (11), trialkylsilyl groups whose alkyl groups each have 1 to 6 carbon atoms, and oxoalkyl groups of 4 to 20 carbon atoms.

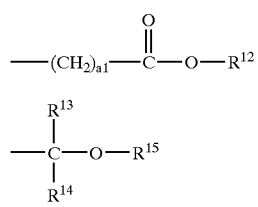

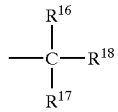

In formula (9), $R^{12}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (11). Exemplary tertiary alkyl groups are tert-butyl, tert-amyl, 1,1-diethylpropyl, 1-ethylcyclo-pentyl, 1-butylcyclopentyl, 1-ethylcyclohexyl, 1-butylcyclo-hexyl, 1-ethyl-2-cyclopentenyl, 1-ethyl-2-cyclohexenyl, and 2-methyl-2-adamantyl. Exemplary trialkylsil, groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter "a1" is an integer of 0 to 6.

In formula (10), $R^{13}$ and $R^{14}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{15}$ is a monovalent hydrocarbon group of 1 to 18 carbon atoms, preferably 1 to 10 carbon atoms, which may have a hetero atom such as oxygen atom, for example, straight, branched or cyclic alkyl groups, and such groups in which some hydrogen atoms are replaced by hydroxyl, alkoxy, oxo, amino or alkylamino groups. Illustrative examples of the substituted alkyl groups are given below.

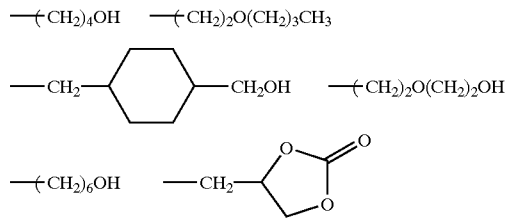

A pair of $R^{13}$ and $R^{14}$, a pair of $R^{13}$ and $R^{15}$, or a pair of $R^{14}$ and $R^{15}$, taken together, may form a ring. Each of $R^{13}$, $R^{14}$ and $R^{15}$ is a straight or branched alkylene group of 1 to 18 carbon atoms, preferably 1 to 10 carbon atoms, when they form a ring.

Illustrative examples of the acid labile groups of formula (9) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyl-oxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyl-oxycarbonylmethyl, 1-ethoxyethoxycarbonylmethyl, 2-tetrahydropyranyloxycarbon.ylmethyl, and 2-tetrahydrofuranyloxycarbonylmethyl.

Substituent groups of the following formulae (9)-1 through (9)-9 are also included.

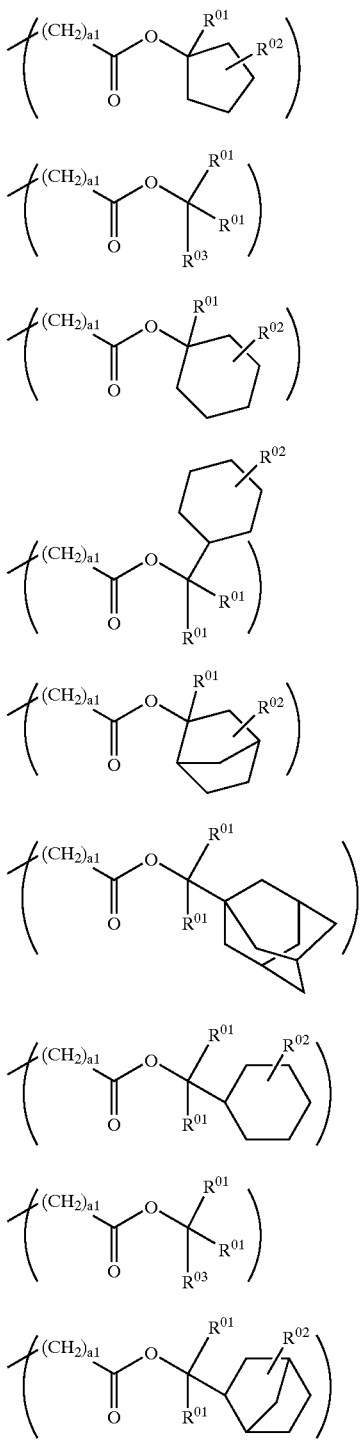

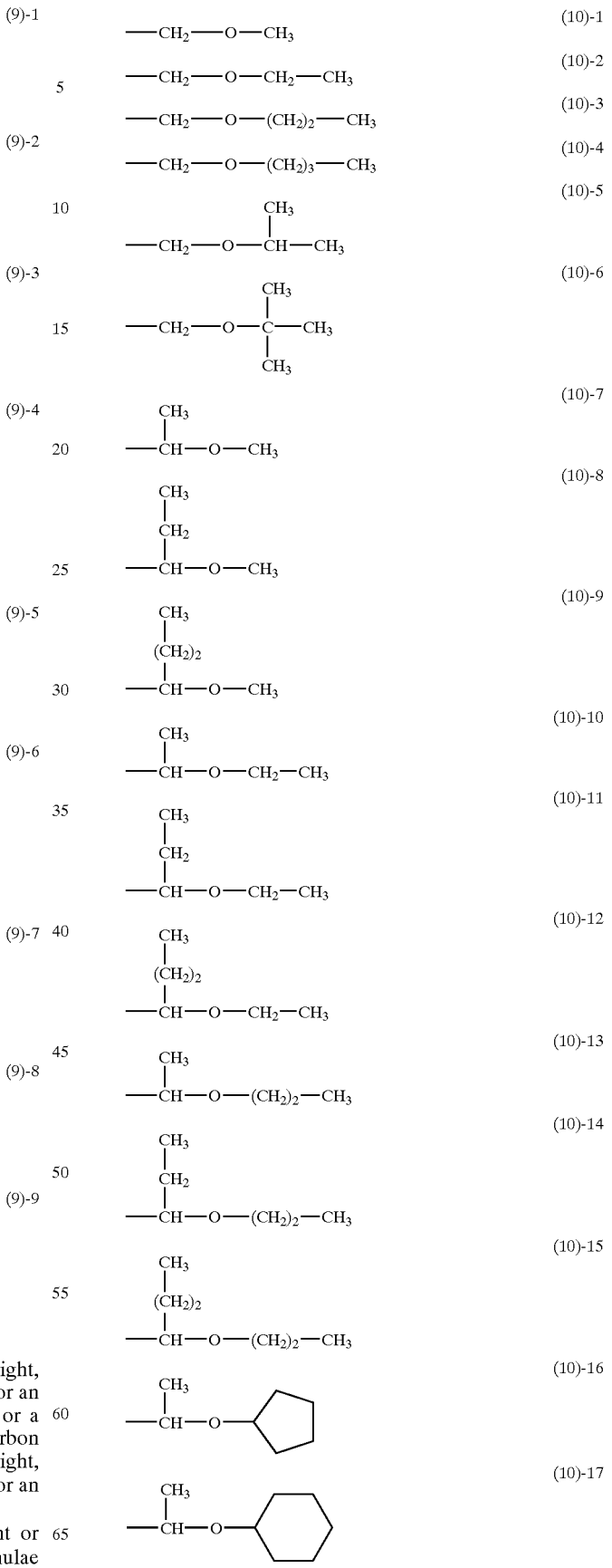

Herein, $R^{01}$ which is identical or different is a straight, branched or cyclic alkyl group of 1 to 10 carbon atoms or an aryl group of 6 to 20 carbon atoms. $R^{02}$ is hydrogen or a straight, branched or cyclic allkyl group of 1 to 10 carbon atoms. $R^{03}$ which is identical or different is a straight, branched or cyclic alkyl group of 2 to 10 carbon atoms or an aryl group of 6 to 20 carbon atoms.

Of the acid labile groups of formula (10), straight or branched groups are exemplified by the following formulae (10)-1 through (10)-23.

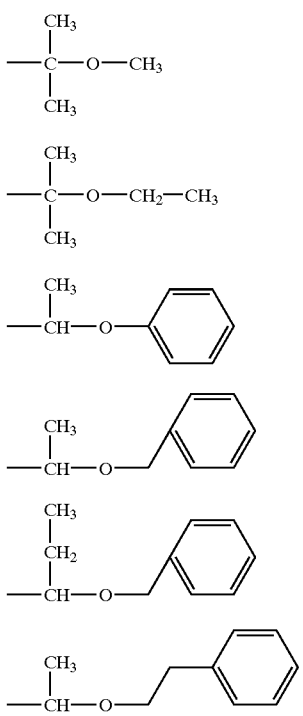

Of the acid labile groups of formula (10), illustrative examples of the cyclic groups include tetrahydrofuran-2-yl, 2-methyltetrahydrofuran-2-yl, tetrahydropyran-2-yl and 2-methyltetrahydropyran-2-yl.

The base resin may be crosslinked within the molecule or between molecules with acid labile groups of the following general formula (10a) or (10b).

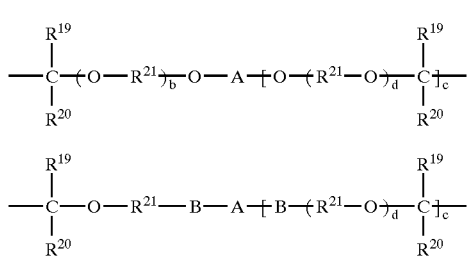

Herein $R^{19}$ and $R^{20}$ each are hydrogen or a straight, branched or cyclic alkyl group of 1 to 8 carbon atoms, or $R^{19}$ and $R^{20}$, taken together, may form a ring, and $R^{19}$ and $R^{20}$ are straight or branched alkylene groups of 1 to 8 carbon atoms when they form a ring; $R^{21}$ is a straight, branched or cyclic alkylene group of 1 to 10 carbon atoms; "b" and "d" each are 0 or an integer of 1 to 10, and preferably 0 or an integer of 1 to 5; "c" is an integer of 1 to 7; "A" is a (c+1)-valent aliphatic or alicyclic saturated hydrocarbon group, aromatic hydrocarbon group or heterocyclic group having 1 to 50 carbon atoms, which may be separated by a hetero atom or in which some of the hydrogen atoms attached to carbon atoms may be substituted with hydroxyl, carboxyl, carbonyl or fluorine; and B is —CO—O—, —NHCO—O— or —NHCONH—.

Preferably, "A" is selected from di- to tetra-valent straight, branched or cyclic alkylene groups; of 1 to 20 carbon atoms, alkyltriyl groups, alkyltetrayol groups and arylene groups of 6 to 30 carbon atoms, which may be separated by a hetero atom and in which some of the hydrogen atoms attached to carbon atoms may be substituted with hydroxyl, carboxyl or acyl groups or halogen atoms. The letter "c" is preferably an integer of 1 to 3.

The crosslinking acetal groups of formulae (10a) and (10b) are exemplified by the following formulae (10)-24 through (10)-35.

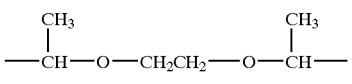

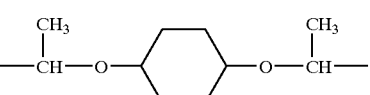

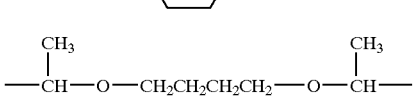

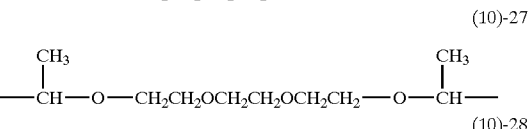

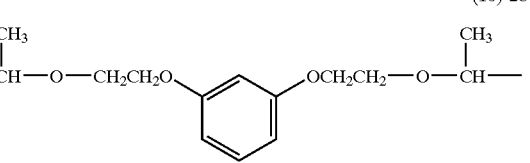

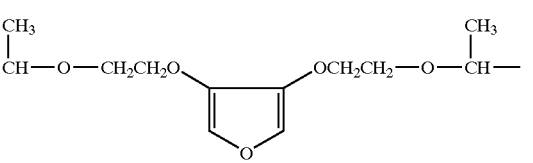

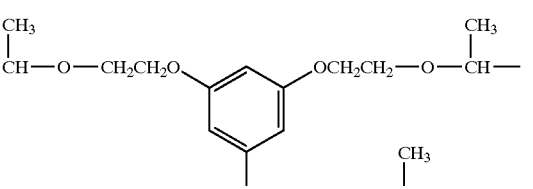

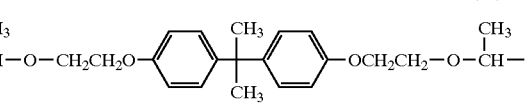

Next, in formula (11), $R^{16}$, $R^{17}$ and $R^{18}$ each are a monovalent hydrocarbon group, typically a straight, branched or cyclic alkyl group of 1 to 20 carbon atoms, which may contain a hetero atom such as oxygen, sulfur, nitrogen or fluorine. A pair of $R^{16}$ and $R^{17}$, $R^{16}$ and $R^{18}$, and $R^{17}$ and $R^{18}$, taken together, may form a ring of 3 to 20 carbon atoms with the carbon atom.

Examples of the tertiary alkyl group represented by formula (11) include tert-butyl, triethylcarbyl, 1-ethylnorbornyl, 1-methylcyclohexyl, 1-ethylcyclopentyl, 2-(2-methyl)adamantyl, 2-(2-ethyl)adamantyl, and tert-amyl.

Other illustrative examples of the tertiary alkyl group are given below as formulae (11)-1 through (11)-18.

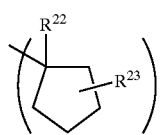 (11)-1
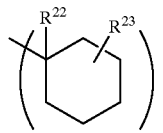 (11)-2
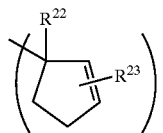 (11)-3
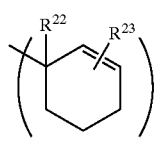 (11)-4
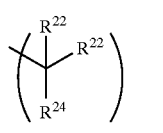 (11)-5
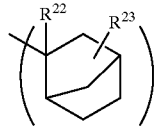 (11)-6
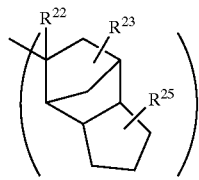 (11)-7
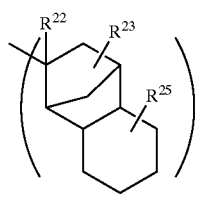 (11)-8
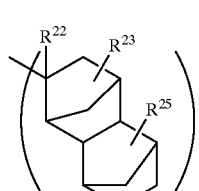 (11)-9
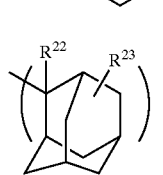 (11)-10
-continued
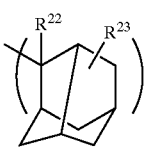 (11)-11
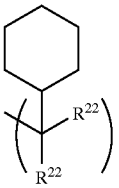 (11)-12
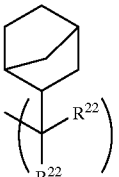 (11)-13
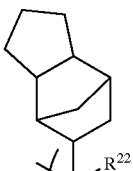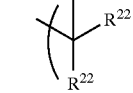 (11)-14
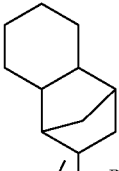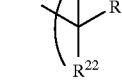 (11)-15
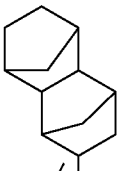 (11)-16
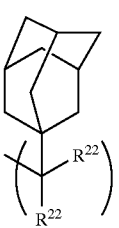 (11)-17

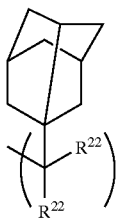

In formulae (11)-1 through (11)-18, $R^{22}$ which may be identical or different is a straight, branched or cyclic alkyl group of 1 to 8 carbon atoms or an aryl group of 6 to 20 carbon atoms, typically phenyl. $R^{23}$ and $R^{25}$ each are hydrogen or a straight, branched or cyclic alkyl group of 1 to 20 carbon atoms. $R^{24}$ is an aryl group of 6 to 20 carbon atoms, typically phenyl.

Further, the polymer may be crosslinked within the molecule or between molecules by incorporating $R^{26}$ which is a divalent or more valent alkylene or arylene group as shown by the following formulae (11)-19 and (11)-20.

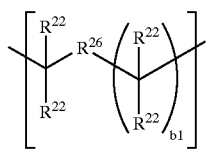
(11)-19

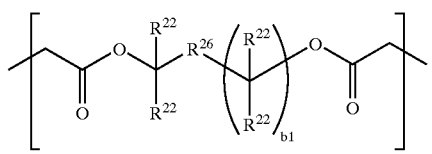
(11)-20

In formulae (11)-19 and (11)-20, $R^{22}$ is as defined above; $R^{26}$ is a straight, branched or cyclic alkylene group of 1 to 20 carbon atoms or an arylene group such as phenylene, which may contain a hetero atom such as an oxygen, sulfur or nitrogen atom; and b1 is an integer of 1 to 3.

Further, $R^{16}$, $R^{17}$ and $R^{18}$ in formula (11) may have a hetero atom such as oxygen, nitrogen or sulfur. Such groups are exemplified below by formulae (12)-1 through (12)-7.

In formulae (9), (10) and (11), $R^{12}$, $R^{15}$ and $R^{18}$ also stand for substituted or unsubstituted aryl groups such as phenyl, p-methylphenyl, p-ethylphenyl and alkoxy-substituted phenyl such as p-methoxyphenyl, and aralkyl groups such as benzyl and phenethyl, alkyl groups of formulae (12)-1 to (12)-5, or oxoalkyl groups of formulae (12)-6 and (12)-9.

(12)-1

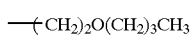
(12)-2

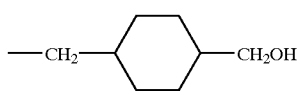
(12)-3

(12)-4

(12)-5

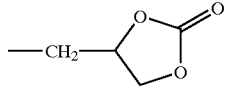
(12)-6

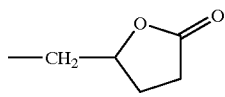
(12)-7

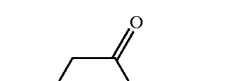
(12)-8

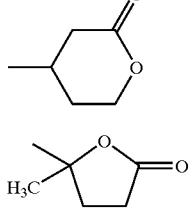
(12)-9

Of the acid labile groups, the trialkylsilyl groups whose alkyl groups each have 1 to 6 carbon atoms include trimethylsilyl, triethylsilyl, and tert-butyldimethylsilyl.

It is noted that the base resin (C) preferably has a weight average molecular weight (Mw) of about 5,000 to about 100,000. A polymer with a Mw of less than 5,000 may have poor film formability and resolution whereas a polymer with a Mw of more than 100,000 may have poor resolution.

Suitable examples of the photoacid generator (D) include onium salts of general formula (13) below, diazomethane derivatives of formula (14), glyoxime derivatives of formula (15), β-ketosulfone derivatives, disulfone derivatives, nitrobenzylsulfonate derivatives, sulfonic acid ester derivatives, and imidoyl sulfonate derivatives.

$$(R^{30})_b M^+ K^-$$  (13)

In the formula, $R^{30}$ is a straight, branched or cyclic alkyl of 1 to 12 carbon atoms, an aryl of 6 to 12 carbon atoms, or an aralkyl of 7 to 12 carbon atoms; $M^+$ is iodonium or sulfonium; $K^-$ is a non-nucleophilic counter-ion; and the letter b is 2 or 3.

Illustrative examples of alkyl groups represented by $R^{30}$ include methyl, ethyl, propyl, butyl, cyclohexyl, 2-oxocyclohexyl, norbornyl, and adamantyl. Exemplary aryl groups include phenyl; alkoxyphenyl groups such as p-methoxyphenyl, m-methoxyphenyl, o-methoxyphenyl, ethoxy-phenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary aralkyl groups include benzyl and phenethyl. Examples of the non-nucleophilic counter-ion represented by $K^-$ include halide ions such as chloride and bromide; fluoroalkylsulfonate ions such as triflate, 2,2,2-trifluoroethanesulfonate, and nonafluorobutanesulfonate; arylsulfonate ions such as tosylate, benzenesulfonate, 4-fluorobenzenesulfonate, and 2,3,4,5,6-pentafluorobenzenesulfonate; and alkylsulfonate ions such as mesylate and butanesulfonate.

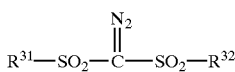
(14)

In the formula, $R^{31}$ and $R^{32}$ are straight, branched or cyclic alkyl or halogenated alkyl groups of 1 to 12 carbon atoms, aryl or halogenated aryl groups of 6 to 12 carbon atoms, or aralkyl groups of 7 to 12 carbon atoms.

Illustrative examples of alkyl groups represented by $R^{31}$ and $R^{32}$ include methyl, ethyl, propyl, butyl, amyl, cyclopentyl, cyclohexyl, norbornyl, and adamantyl. Exemplary halogenated alkyl groups include trifluoromethyl, 2,2,2-trifluoroethyl, 2,2,2-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorobenzene, chlorobenzene, and 2,3,4,5,6-pentafluorobenzene. Exemplary aralkyl groups include benzyl and phenethyl.

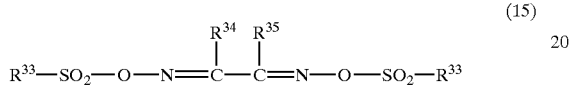

(15)

In the formula, $R^{33}$, $R^{34}$, and $R^{35}$ are straight, branched or cyclic alkyl or halogenated alkyl groups of 1 to 12 carbon atoms, aryl or halogenated aryl groups of 6 to 12 carbon atoms, or aralkyl groups of 7 to 12 carbon atoms. $R^{34}$ and $R^{35}$ may together form a cyclic structure with the proviso that if they form a cyclic structure, each :is a straight or branched alkylene group of 1 to 6 carbon atoms.

The alkyl, halogenated alkyl, aryl, halogenated aryl, and aralkyl groups represented by $R^{33}$, $R^{34}$, and $R^{35}$ are exemplified by the same groups as mentioned above for $R^{31}$ and $R^{32}$. Examples of alkylene groups represented by $R^{34}$ and $R^{35}$ include methylene, ethylene, propylene, butylene, and hexylene.

Illustrative examples of the photoacid generator include:

onium salts such as diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis (p-tert-butoxyphenyl)phenylsulfonium p-toluenesulfonate, tris (p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, and dicyclohexylphenylsulfonium p-toluenesulfoneLte;

diazomethane derivatives such as bis(benzenesulfonyl)diazomethane, bis(p-toluenesulfonyl)diazomethane, bis(xylenesulfonyl)diazomethane, bis(cyclohexylsulfonyl)-diazomethane, bis(cyclopentylsulfonyl)diazomethane, bis(n-butylsulfonyl) diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)-diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexyl-sulfonyl-1-(tert-amylsulfonyl)diazomethane, and 1-tert-amylsulfonyl-1-(tert-butylsulfonyl)diazomethane;

glyoxime derivatives such as bis-O-(p-toluene-sulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butane-sulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethyiglyoxime, bis-O-(trifluoromethanesulfonyl)-α-dimethylglyoxime, bis-O-(1,1,1-trifluoroethanesulfonyl)-α-dimethyl-glyoxime, bis-O-(tert-butanesulfonylr)-α-dimethylglyoxime, bis-O-(perfluorooctanesulfonyl)-α-dimethylglyoxime, bis-O-(cyclohexanesulfonyl)-α-ddimethyiglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

β-ketosulfone derivatives such as 2-cyclohexylcarbonyl-2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and imidoyl sulfonate derivatives such as phthalimidoyl triflate, phthalimidoyl tosylate, 5-norbornene-2,3-dicarboxyimidoyl triflate, 5-norbornene-2,3-dicarboxyimidoyl tosylate, and 5-norbornene-2,3-dicarboxyimidoyl n-butylsulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, and tris(p-tert-butoxyphenyl)sulfonium p-toluenesulfonate; diazomethane derivatives such as bis(benzene,sulfonyl)diazomethane, bis(p-toluenesulfonyl)diazomethane, bis(cyclohexylsulfonyl) diazomethane, bis(n-butylsulfonyl)dliazomethane, bis(isobutylsulfonyl)diazomethane, bis(sec-butylsulfonyl)-diazomethane, bis(n-propylsulfonyl)diazomethane, bis(isopropylsulfonyl)diazomethane, and bis(tert-butylsulfonyl)-diazomethane; and glyoxime derivatives such as bis-O-(p-toluenesulfonyl)-α-dimethylglyoxime and bis-O-(n-butane-sulfonyl)-α-dimethylglyoxime; and naphthoquinone-diazidosulfonate derivatives. These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is preferably added in an amount of about 0.2 to 50 parts by weight, and especially about 0.5 to 40 parts by weight, per 100 parts by weight of the entire base resin. At less than 0.2 part, the amount of acid generated during exposure may be too small, resulting in poor sensitivity and resolution. The addition of more than 50 parts may lower the transmittance of the resist and result in a poor resolution.

The dissolution inhibitor (E) is a compound with a molecular weight of up to 3,000 which changes its solubility in an alkaline developer under the action of an acid. Typically, a compound obtained by partially or entirely substituting acid labile substituents on a phenol or carboxylic acid derivative having a molecular weight of up to 2,500 is added as the dissolution inhibitor.

Examples of the phenol or carboxylic acid derivative having a molecular weight of up to 2,500 include bisphenol A, bisphenol H, bisphenol S, 4,4-bis(4'-hydroxyphenyl) valeric acid, tris(4-hydroxyphenyl)methane, 1,1,1-tris(4'-hydroxyphenyl)ethane, 1,1,2-tris(4'-hydroxyphenyl)ethane, phenolphthalein, and thimolphthalein. The acid labile substituents are the same as exemplified for $R^4$.

Illustrative, non-limiting, examples of the dissolution inhibitors which are useful herein include bis(4-(2'-tetrahydropyranyloxy)phenyl)methane,
bis(4-(2'-tetrahydrofuranyloxy)phenyl)methane,
bis(4-tert-butoxyphenyl)methane,
bis(4-tert-butoxycarbonyloxyphenyl)methane,
bis(4-tert-butoxycarbonylmethyloxyphenyl)methane,
bis(4-(1'-ethoxyethoxy)phenyl)methane,
bis(4-(1'-ethoxypropyloxy)phenyl)methane,
2,2-bis(4'-(2"-tetrahydropyranyloxy))propane,
2,2-bis(4'-(2"-tetrahydrofuranyloxy)phenyl)propane,
2,2-bis(4'-tert-butoxyphenyl)propane,
2,2-bis(4'-tert-butoxycarbonyloxyphenyl)propane,
2,2-bis(4-tert-butoxycarbonylmethyloxyphenyl)propane,
2,2-bis(4'-(1"-ethoxyethoxy)phenyl)propane,
2,2-bis(4'-(1"-ethoxypropyloxy)phenyl)propane,
tert-butyl 4,4-bis(4'-(2"-tetrahydropyranyloxy)phenyl)-valerate,
tert-butyl 4,4-bis(4'-(2"-tetrahydrofuranyloxy)phenyl)-valerate,
tert-butyl 4,4-bis(4'-tert-butoxyphenyl)valerate,
tert-butyl 4,4-bis(4-tert-butoxycarbonyloxyphenyl)valerate,
tert-butyl 4,4-bis(4'-tert-butoxycarbonylmetlhyloxyphenyl)-valerate,
tert-butyl 4,4-bis(4'-(1"-ethoxyethoxy)phenyl)valerate,
tert-butyl 4,4-bis(4'-(1"-ethoxypropyloxy)phenyl)valerate,
tris(4-(2'-tetrahydropyranyloxy)phenyl)methane,
tris(4-(2'-tetrahydrofuranyloxy)phenyl)methane,
tris(4-tert-butoxyphenyl)methane,
tris(4-tert-butoxycarbonyloxyphenyl)methane,
tris(4-tert-butoxycarbonyloxymethylphenyl)methane,
tris(4-(1'-ethoxyethoxy)phenyl)methane,
tris(4-(1'-ethoxypropyloxy)phenyl)methane,
1,1,2-tris(4'-(2"-tetrahydropyranyloxy)phenyl)ethane,
1,1,2-tris(4'-(2"-tetrahydrofuranyloxy)phenyl)ethane,
1,1,2-tris(4'-tert-butoxyphenyl)ethane,
1,1,2-tris(4'-tert-butoxycarbonyloxyphenyl)ethane,
1,1,2-tris(4'-tert-butoxycarbonylmethyloxyphenyl)ethane,
1,1,2-tris(4'-(1'-ethoxyethoxy)phenyl)ethane, and
1,1,2-tris(4'-(1'-ethoxypropyloxy)phenyl)ethane.

An appropriate amount of the dissolution inhibitor is up to 20 parts, and especially up to 15 parts by weight per 100 parts by weight of the solids in the resist composition. With more than 20 parts of the dissolution inhibitor, the resist composition becomes less heat resistant because of an increased content of monomer components.

Formulated in the negative resist composition is an crosslinker (F) which forms a crosslinked structure under the action of acid. Typical crosslinkers are compounds having at least two hydroxymethyl, alkoxymelthyl, epoxy or vinyl ether groups within a molecule. Substituted glycoluril derivatives, urea derivatives, and hexa(methoxy-methyl) melamine compounds are suitable as the crosslinker. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred crosslilnkers are 1,3,5,7-tetraalkoxymethylglycolurils such as 1,3,5,7-tetramethoxymethylglycoluril, 1,3,5,7-tetrahydroxymethylglycoluril, 2,6-dihydroxymethyl-p-cresol, 2,6-dihydroxymethylphenol, 2,2', 6,6'-tetrahydroxymethyl-bisphenol A, 1,4-bis[2-(2-hydroxypropyl)]benzene, N,N,N',N'-tetramethoxymethylurea, and hexamethoxymethyl-melamine. In the resist composition, an appropriate amount of the crosslinker is, though not limited thereto, about 1 to 25 parts, and especially about 5 to 20 parts by weight per 100 parts by weight of the solids in the composition. The crosslinkers may be used alone or in admixture of two or more.

In addition to the inventive basic compound, one or more of commonly used bases may be employed in the inventive resist composition. Examples of suitable conventional basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamiLne, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylanine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N- dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methyl-pyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-beearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, truisopropanolamine, 2,2'-iminodiethanol, 2-amino-ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]-piperazine, piperidine ethanol, 1-(2-hydroxyethyl)-pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxy-ethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formulas (B)-100 and (B)-101 may also be included.

(B)-100

(B)-101

In the formulas, $R^{41}_1$ $R^{42}$ $R^{43}$ $R^{47}$ and $R^{48}$ independently straight, branched or cyclic alkylenes of 1 to are 20 carbon atoms; $R^{44}$, $R^{45}$, $R^{46}$, $R^{49}$ and $R^{50}$ are hydrogen, alkyls of 1 to 20 carbon atoms, or amino; $R^{44}$ and $R^{45}$, $R^{45}$ and $R^{46}$, $R^{44}$ and $R^{46}$, $R^{44}$ with $R^{45}$ and $R^{46}$, and $R^{49}$ and $R^{50}$ may bond together to form rings; and S, T and U are each integers from 0 to 20, with the proviso that hydrogen is excluded from $R^{44}$, $R^{45}$, $R^{46}$ $R^{49}$ and $R^{50}$ when S, T and U are equal to 0.

The alkylene groups represented by $R^{41}$, $R^{42}$, $R^{43}$, $R^{47}$ and $R^{48}$ preferably have 1 to 20 carbon atoms, more preferably 1 to 10 carbon atoms, and most preferably 1 to 8 carbon atoms. Examples include methylene, ethylene, n-propylene, isopropylene, n-butylene, isobutylene, n-pentylene, isopentylene, hexylene, nonylene, decylene, cyclopentylene, and cyclohexylene.

The alkyl groups represented by $R^{44}$, $R^{45}$, $R^{46}_1$, $R^{49}$ and $R^{50}$ preferably have 1 to 20 carbon atoms, more preferably 1 to 8 carbon atoms, and most preferably 1 to 6 carbon atoms, and may be straight, branched or cyclic. Examples include methyl, ethyl, n-propyl, isopropyl, n-butyl, isobutyl, tert-butyl, n-pentyl, isopentyl, hexyl, nonyl, decyl, dodecyl, tridecyl, cyclopentyl, and cyclohexyl.

Where $R^{44}$ and $R^{45}$, $R^{45}$ and $R^{46}$, $R^{44}$ and $R^{46}$, $R^{44}$ with $R^{45}$ and $R^{46}$, and $R^{49}$ and $R^{50}$ form rings, the rings preferably have 1 to 20 carbon atoms, more preferably 1 to 8 carbon atoms, and most preferably 1 to 6 carbon atoms, andimay have pendant alkyl groups of 1 to 6 carbon atoms, and especially 1 to 4 carbon atoms.

S, T, and U are each integers from 0 to 20, preferably from 1 to 10, and more preferably from 1 to 8.

Illustrative examples of the compounds of formulas (B)-100 and (B)-101 include tris{2-(methoxymethoxy)- ethyl}amine, tris{2-(methoxyethoxy)ethyl}amine, tris[2-{(2-methoxyethoxy)methoxy}ethyl]amine, tris{2-(2-methoxyethoxy)-ethyl}amine, tris{2-(1-methoxyethoxy)ethyl}amine, tris{2-(1-ethoxyethoxy)ethyl}amine, tris{2-(1-ethoxypropoxy)-ethyl}amine, tris[2-{(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, and 1-aza-18-crown-6.

The resist composition of the invention may include, as an optional ingredient, a surfactant which is commonly used for improving the coating characteristics. Optional ingredients may be added in conventional amounts so long as this does not compromise the objects of the invention.

A nonionic surfactant is preferred, examples of which include perfluoroalkyl polyoxyethylene ethanols, fluorinated alkyl esters, perfluoroalkylamine oxides, and fluorinated organosiloxane compounds. Illustrative examples include Florade FC-430 and FC-431 from Sumitomo 3M Ltd., Surflon S-141, S-145, S-381 and S-383 from Asahi Glass Co., Ltd., Unidyne DS-401, DS-403, and DS-451 from Daikin Industries Ltd., Megaface F-8151, F-171, F-172, F-173 and F-177 from Dainippon Ink & Chemicals, Inc., and X-70-092 and X-70-093 from Shin-Etsu Chemical Co., Ltd. Preferred surfactants include Florade FC-430 from Sumitomo 3M Ltd. and X-70-093 from Shin-Etsu Chemical Co., Ltd. Also, nonionic surfactants of various hydrocarbon chains may be added for improving the wetting of resist with a developer.

Pattern formation using the resist composition of the invention may be carried out by a known lithographic technique. For example, the resist composition may be applied onto a substrate such as a silicon wafer by spin coating or the like to form a resist film having a thickness of 0.1 to 1.0 μm, which is then pre-baked on a hot plate at 60 to 200° C. for 10 seconds to 10 minutes, and preferably at 80 to 150° C. for ½ to 5 minutes. A patterning mask having the desired pattern may then be placed over the resist film, and the film exposed through the mask to an electron beam or to high-energy radiation such as deep-UV rays having a wavelength below 300 nm, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for ½ to 3 minutes. Finally, development may be carried out using as the developer an aqueous alkali solution, such as 0.1 to 5%, and preferably 2 to 3%, tetramethylammonium hydroxide (TMAH), this being done by a conventional method such as dipping, puddling, or spraying for a period of 10 seconds to 3 minutes, and preferably 30 seconds to 2 minutes. These steps result in the formation of the desired pattern on the substrate. Of the various types of high-energy radiation that may be used, the resist composition of the invention is best suited to fine pattern formation with, in particular, deep-UV rays having a wavelength of 254 to 120 nm, an excimer laser, especially ArF excimer laser (193 nm), $F_2$ excimer laser (157 nm), $Kr_2$ excimer laser (146 nm), KrAr excimer laser (134 nm) or $Ar_2$ excimer laser (126 nm), soft x-rays of 13 nm, 11 nm and 8 nm, x-rays, or an electron beam. The desired pattern may not be obtainable outside the upper and lower limits of the above range.

The resist composition comprising the amine compound according to the invention is effective for preventing a resist film from thinning and for expanding the focus margin while achieving an improved resolution.

EXAMPLE

Synthesis Examples and Examples are given below for illustrating the invention, but are not to be construed as limiting the invention thereto.

Synthesis Examples

Amine compounds according to the invention were synthesized by the methods described below.

Synthesis Example 1

Synthesis of 3-(diethylamino)propiononitrile (Amine 1)

At 20 to 30° C., 5.31 g of acrylonitrile was added to 7.31 g of diethylamine. The mixture was allowed to stand for 16 hours, obtaining 12.2 g (quantitative yield) of 3-(diethylamino)propiononitrile.

Synthesis Example 2

Synthesis of N,N-bis (2-hydroxyethyl)-3-aminopropiononitrile (Amine 2)

By the same procedure as Synthesis Example 1 except that diethanolamine was used instead of diethylamine, there was obtained N,N-bis(2-hydroxyethyl)-3-aminopropiononitrile.

Synthesis Example 3

Synthesis of N,N-bis( 2-acetoxyethyl)-3-aminopiropiononitrile (Amine 3)

At 20 to 30° C., 22.3 g of acetic anhydride was added to a mixture of 15.0 g of N,N-bis(2-hydroxyethyl)-3-aminopropiononitrile, 25.0 g of triethylamine, 50 mg of 4-dimethylaminopyridine and 50 g of dry tetrahydrofuran. The mixture was stirred for 10 hours whereupon 10 g of water was added to stop the reaction. The reaction solution was allowed to separate. The organic layer was washed with water and concentrated in vacuum. Purification by vacuum distillation yielded 20.9 g of N,N-bis(2-acetoxyethyl)-3-aminopropiononitrile (boiling point: 136° C./30 Pa, yield: 89%).

IR (thin film): ν=2960, 2838, 2249, 1738, 1458, 1373, 1240, 1043 cm$^{-1}$ $^1$H-NMR (300 MHz in $CDCl_3$): δ=2.03 (6H, s), 2.44 (2H, t, J=6.9 Hz), 2.81 (4H, t, J=6.0 Hz), 2.90 (2H, t, J=6.9 Hz), 4.10 (4H, t, J=6.0 Hz)

Synthesis Example 4

Synthesis of N,N-bis(2-formyloxyethyl)-3-aminopropiononitrile (Amine 4)

A mixture of 15.0 g of N,N-bis(2-hydroxyethyl)-3-aminopropiononitrile and 150 g of formic acid was stirred for 10 hours at 700° C. The reaction solution was concentrated in vacuum, diluted with ethyl acetate, washed with saturated sodium bicarbonate in water, and concentrated in vacuum again, obtaining N,N-bis(2-formyloxyethyl)-3-aminopropiononitrile.

Synthesis Example 5

Synthesis of N,N-bis(2-methoxyethyl)-3-aminopropiononitrile (Amine 5)

By following the same procedure as Synthesis Example 1 except that bis(2-methoxyethyl)amine was used, instead of diethylamine, N,N-bis(2-methoxyethyl)-3-aminopropiononitrile was obtained (boiling point: 87° C./60 Pa, yield: 91%).

IR (thin film): ν=2927, 2877, 2825, 2247, 1458, 1363, 1196, 1149, 1119, 1070, 1012, 960 cm$^{-1}$ $^1$H-NMR (300 MHz in CDCl$_3$): δ=2.46 (2H, t, J=6.9 Hz), 2.74 (4H, t, J=5.6 Hz), 2.94 (2H, t, J=6.9 Hz), 3.31 (6H, s), 3.44 (4H, t, J=5.6 Hz)

Synthesis Example 6

Synthesis of N,N-bis[2-(methoxymethoxy)ethyl]-3-aminopropiononitrile (Amine 6)

By following the same procedure as Synthesis Example 1 except that bis[2-(methoxymethoxy)ethyl]amine was used instead of diethylamine, N,N-bis[2-(methoxymethoxy)ethyl]-3-aminopropiononitrile was obtained.

Synthesis Example 7

Synthesis of methyl N-(2-cyanoethyl)-N-(2-methoxyethyl)-3-aminopropionate (Amine 7)

At 20 to 30° C., 11.4 g of methyl acrylate was added to 10.0 g of 2-methoxyethylamine, which was allowed to stand for 2 hours. Then 15.0 g of acrylonitrile was added to the reaction solution, which was heated at 70° C. for 20 hours. Vacuum concentration yielded methyl N-(2-cyanoethyl)-N-(2-methoxyethyl)-3-aminopropionate.

Synthesis Example 8

Synthesis of methyl N-(2-cyanoethyl)-N-(2-hydroxyethyl)-3-aminopropionate (Amine 8)

By following the same procedure as Synthesis Example 7 except that 2-aminoethanol was used instead of 2-methoxyethylamine, methyl N-(2-cyanoethyl)-N-(2-hydroxy-ethyl)-3-aminopropionate was synthesized.

Synthesis Example 9

Synthesis of methyl N-(2-acetoxyethyl)-N-(2-cyanoethyl)-3-aminopropionate (Amine 9)

By following the same procedure as Synthesis Example 3 except that methyl N-(2-cyanoethyl)-N-(2-hydroxyethyl)-3-aminopropionate was used instead of N,N-bis(2-hydroxyethyl)-3-aminopropiononitrile, methyl N-(2-acetoxyethyl)-N-(2-cyanoethyl)-3-aminopropionate was synthesized.

Synthesis Example 10

Synthesis of N-(2-cyanoethyl)-N-ethyl-3-aminopropiononitrile (Amine 10)

At 20 to 30° C., 30 g of acrylonitrile was added to 10.0 g of ethylamine, which was heated at 70° C. and stirred at the temperature for 100 hours. Purification by vacuum distillation yielded N-(2-cyanoethyl)-N-ethyl-3-aminopropiononitrile.

Synthesis Example 11

Synthesis of N-(2-cyanoethyl)-N-(2-hydroxyethyl)-3-aminopropiononitrile (Amine 11)

By following the same procedure as Synthesis Example 10 except that 2-aminoethanol was used instead of ethylamine, N-(2-cyanoethyl)-N-(2-hydroxyethyl)-3-aminopropiononitrile was synthesized.

Synthesis Example 12

Synthesis of N-(2-acetoxyethyl)-N-(2-cyanoethyl)-3-aminopropiononitrile (Amine 12)

By following the same procedure as Synthesis Example 3 except that N-(2-cyanoethyl)-N-(2-hydroxyethyl)-3-aminopropiononitrile was used instead of N,N-bis(2-hydroxyethyl)-3-aminopropiononitrile, N-(2-acetoxyethyl)-N-(2-cyanoethyl)-3-aminopropiononitrile was synthesized.

IR (thin film): ν=2960, 2848, 2249, 1736, 1466, 1423, 1373, 1240, 1144, 1041 cm$^{-1}$ $^1$H-NMR (300 MHz in CDCl$_3$): δ=2.05 (3H, s), 2.47 (4H, t, J=6.8 Hz), 2.82 (2H, t, J=5.6 Hz), 2.92 (4H, 1:, J=6.8 Hz), 4.12 (2H, t, J=5.6 Hz)

Synthesis Example 13

Synthesis of N-(2-cyanoethyl)-N-(2-formyloxyethyl)-3-aminopropiononitrile (Amine 13)

By following the same procedure as Synthesis Example 4 except that N-(2-cyanoethyl)-N-(2-hydroxyethyl)-3-aminopropiononitrile was used instead of N,N-bis(2-hydroxyethyl)-3-aminopropiononitrile, N-(2-cyanoethyl)-N-(2-formyloxy-ethyl)-3-aminopropiononitrile was synthesized.

Synthesis Example 14

Synthesis of N-(2-cyanoethyl)-N-(2-methoxyethyl)-3-aminopropiononitrile (Amine 14)

By following the same procedure as Synthesis Example 10 except that 2-methoxyethylamine was used instead of ethylamine, N-(2-cyanoethyl)-N-(2-methoxyethyl)-3-aminopropiononitrile was synthesized (boiling point: 130° C./19 Pa).

IR (thin film): ν=2931, 2877, 2845, 2247, 1464, 1421, 1367, 1267, 1252, 1198, 1146, 1117, 1076, 1043, 968 cm$^{-1}$ $_1$H-NMR (300 MHz in CDCl$_3$): δ=2.47 (4H, t, J=6.9 Hz), 2.76 (2H, t, J=5.3 Hz), 2.99 (4H, t, J=6.9 Hz), 3.32 (3H, s), 3.45 (2H, t, J=5.3 Hz)

Synthesis Example 15

Synthesis of N-(2-cyanoethyl)-N-[2-(methoxymethoxy)ethyl]-3-aminopropiononitrile (Amine 15)

By following the same procedure as Synthesis Example 10 except that 2-(methoxymethoxy)ethylamine was used instead of ethylamine, N-(2-cyanoethyl)-N-[2-(methoxymethoxy)ethyl]-3-aminopropiononitrile was synthesized.

Synthesis Example 16

Synthesis of N-(2-cyanoethyl)-N-(3-hydroxy-1-propyl)-3-aminopropiononitrile (Amine 16)

By following the same procedure as Synthesis Example 10 except that 3-hydroxy-1-propylamine was used instead of ethylamine, N-(2-cyanoethyl)-N-(3-hydroxy-1-propyl)-3-aminopropiononitrile was synthesized.

Synthesis Example 17

Synthesis of N-(3-acetoxy-1-propyl)-N-(2-cyanoethyl)-3-aminopropiononitrile (Amine 17)

By following the same procedure as Synthesis Example 3 except that N-(2-cyanoethyl)-N-(3-hydroxy-1-propyl)-3- aminopropiononitrile was used instead of N,N-bis(2-hydroxyethyl)-3-aminopropiononitrile, N-(3-acetoxy-1-propyl)-N-(2-cyano-ethyl)-3-aminopropiononitrile was synthesized (boiling point: 173° C./20 Pa, yield: 95%).

IR (thin film): ν=2960, 2839, 2247, 1734, 1466, 1423, 1367, 1246, 1138, 1087, 1045 cm$^{-1}$ $^1$H-NMR (270 MHz in CDCl$_3$): δ=1.77 (2H, tt, J=7.2, 6.2 Hz), 2.03 (3H, s), 2.46 (4H, t, J=6.9 Hz), 2.62 (2H, t, J=7.2 Hz), 2.85 (4H, t, J=6.9 Hz), 4.13 (2H, t, J=6.2 Hz)

Synthesis Example 18

Synthesis of N-(2-cyanoethyl)-N-(3-formyloxy-1-propyl)-3-aminopropiononitrile (Amine 18)

By following the same procedure as Synthesis Example 4 except that N-(2-cyanoethyl)-N-(3-hydroxy-1-propyl)-3-aminopropiononitrile was used instead of N,N-bis(2-hydroxy-ethyl)-3-aminopropiononitrile, N-(2-cyanoethyl)-N-(3-formyloxy-1-propyl)-3-aminopropiononitrile was synthesized.

Synthesis Example 19

Synthesis of N-(2-cyanoethyl)-N-tetrahydrofurfuryl-3-aminopropiononitrile (Amine 19)

By following the same procedure as Synthesis Example 10 except that tetrahydrofurfurylamine was used instead of ethylamine, N-(2-cyanoethyl)-N-tetrahydrofurfuryl-3-aminopropiononitrile was synthesized.

Synthesis Example 20

Synthesis of N,N-bis(2-cyanoethyl)-3-aminopropiononitrile (Amine 20)

At 0° C., 50 g of acrylonitrile was added to 10 g of 28% aqueous ammonia, which was heated at 100° C. and stirred at the temperature for 100 hours. The reaction solution was concentrated in vacuum and then distilled in vacuum for purification, obtaining N,N-bis(2-cyanoethyl)-3-aminopropiononitrile.

Synthesis Example 21

Synthesis of diethylaminoacetonitrile (Amine 21)

At 0° C., 12.0 g of bromoacetonitrile was added to 14.6 g of diethylamine. The mixture was heated to 20° C. over 10 hours. Ethyl acetate was added to the reaction mixture, and the resulting solids were filtered off. Distillation yielded diethylaminoacetonitrile (boiling point: 170° C., yield: 90%).

IR (thin film): ν=2976, 2222, 1461, 1389, 1322, 1206, 1093, 984 cm$^{-1}$ $^{13}$C-NMR (75 MHz in CDCl$_3$): δ=12.6, 40.5, 47.9, 114.8

Synthesis Example 22

Synthesis of N,N-bis(2-hydroxyethyl) aminoacetonitrile (Amine 22)

By following the same procedure as Synthesis Example 21 except that diethanolamine was used instead of diethylamine, N,N-bis(2-hydroxyethyl)aminoacetonitrile was synthesized.

Synthesis Example 23

Synthesis of N,N-bis(2-acetoxyethyl) aminoacetonitrile (Amine 23)

By following the same procedure as Synthesis Example 3 except that N,N-bis(2-hydroxyethyl)aminoacetonitrile was used instead of N,N-bis(2-hydroxyethyl)-3-aminopropiononitrile, N,N-bis(2-acetoxyethyl) aminoacetonitrile was synthesized (boiling point: 120° C./25 Pa).

IR (thin film): ν=2962, 2839, 2222, 1740, 1651, 1433, 1371, 1234, 1045 cm$^{-1}$ $^1$H-NMR (300 MHz in CDCl$_3$): δ=2.04 (6H, s), 2.83 (4H, t, J=5.5 Hz), 3.68 (2H, s), 4.14 (4H, t, J=5.5 Hz)

Synthesis Example 24

Synthesis of N,N-bis(2-formyloxyethyl) aminoacetonitrile (Amine 24)

By following the same procedure as Synthesis Example 4 except that N,N-bis(2-hydroxyethyl)aminoacetonitrile was used instead of N,N-bis(2-hydroxyethyl)-3-aminopropiononitrile, N,N-bis(2-formyloxyethyl) aminoacetonitrile was synthesized.

Synthesis Example 25

Synthesis of N,N-bis(2-methoxyethyl) aminoacetonitrile (Amine 25)

By following the same procedure as Synthesis Example 21 except that bis(2-methoxyethyl)amine was used instead of diethylamine, N,N-bis(2-methoxyethyl)aminoacetonitrile was synthesized.

Synthesis Example 26

Synthesis of N,N-bis[2-(methoxymethoxy)ethyl] aminoaceto-nitrile (Amine 26)

By following the same procedure as Synthesis Example 21 except that bis[2-(methoxymethoxy)ethyl]amine was used instead of diethylamine, N,N-bis[2-(methoxymethoxy) ethyl]-aminoacetonitrile was synthesized.

Synthesis Example 27

Synthesis of methyl N-cyanomethyl-N-(2-methoxyethyl)-3-aminopropionate (Amine 27)

At 20 to 30° C., 11.4 g of methyl acrylate was added to 10.0 g of 2-methoxyethylamine, which was allowed to stand for 2 hours. Then 7.92 g of bromoacetonitrile was added to the reaction solution, which was heated at 70° C. for 20 hours. The reaction solution was diluted with ethyl acetate and the resulting solids were filtered off. Vacuum concentration yielded methyl N-cyanomethyl-N-(2-methoxyethyl)-3-aminopropionate.

Synthesis Example 28

Synthesis of methyl N-cyanomethyl-N-(2-hydroxyethyl)-3-aminopropionate (Amine 28)

By following the same procedure as Synthesis Example 27 except that 2-aminoethanol was used instead of 2-methoxy-ethylamine, methyl N-cyanomethyl-N-(2-hydroxyethyl)-3-aminopropionate was synthesized.

Synthesis Example 29

Synthesis of methyl N-(2-acetoxyethyl)-N-cyanomethyl-3-aminopropionate (Amine 29)

By following the same procedure as Synthesis Example 3 except that methyl N-cyanomethyl-N-(2-hydroxyethyl)-3- aminopropionate was used instead of N,N-bis(2-hydroxyethyl)-3-aminopropiononitrile, methyl N-(2-acetoxyethyl)-N-cyano-methyl-3-aminopropionate was synthesized.

Synthesis Example 30

Synthesis of N-cyanomethyl-N-(2-hydroxyethyl)aminoaceto-nitrile (Amine 30)

At 20 to 30° C., 12.0 g of bromoacetonitrile was added to a mixture of 6.11 g of ethanolamine and 20.2 g of triethylamine. The mixture was heated at 70° C. for 20 hours. The reaction solution was diluted with ethyl acetate and the resulting solids were filtered off. Vacuum concentration yielded N-cyanomethyl-N-(2-hydroxyethyl) aminoacetonitrile.

Synthesis Example 31

Synthesis of N-(2-acetoxyethyl)-N-(cyanomethyl)aminoaceto-nitrile (Amine 31)

By following the same procedure as Synthesis Example 3 except that N-cyanomethyl-N-(2-hydroxyethyl)aminoacetonitrile was used instead of N,N-bis(2-hydroxyethyl)-3-aminopropiononitrile, N-(2-acetoxyethyl)-N-(cyanomethyl)-aminoacetonitrile was synthesized.

Synthesis Example 32

Synthesis of N-cyanomethyl-N-(2-formyloxyethyl)aminoacetonitrile (Amine 32)

By following the same procedure as Synthesis Example 4 except that N-cyanomethyl-N-(2-hydroxyethyl)aminoacetonitrile was used instead of N,N-bis(2-hydroxyethyl)-3-aminopropiononitrile, N-cyanomethyl-N-(2-formyloxyethyl)-aminoacetonitrile was synthesized.

Synthesis Example 33

Synthesis of N-cyanomethyl-N-(2-methoxyethyl)aminoacetonitrile (Amine 33)

By following the same procedure as Synthesis Example 30 except that (2-methoxyethyl)amine was used instead of ethanolamine, N-cyanomethyl-N-(2-methoxyethyl)aminoacetonitrile was synthesized.

Synthesis Example 34

Synthesis of N-cyanomethyl-N-[2-(methoxymethoxy)ethyl]-aminoacetonitrile (Amine 34)

By following the same procedure as Synthesis Example 30 except that [2-(methoxymethoxy)ethyl]amine was used instead of ethanolamine, N-cyanomethyl-N-[2-(methoxymethoxy)ethyl]aminoacetonitrile was synthesized.

Synthesis Example 35

Synthesis of N-cyanomethyl-N-(3-hydroxy-1-propyl)aminoacetonitrile (Amine 35)

By following the same procedure as Synthesis Example 30 except that 3-amino-1-propanol was used instead of ethanolamine, N-cyanomethyl-N-(3-hydroxy-1-propyl) amino-acetonitrile was synthesized.

Synthesis Example 36

Synthesis of N-(3-acetoxy-1-propyl)-N-(cyanomethyl)amino-acetonitrile (Amine 36)

By following the same procedure as Synthesis Example 3 except that N-cyanomethyl-N-(3-hydroxy-1-propyl) aminoacetonitrile was used instead of N,N-bis(2-hydroxyethyl)-3-aminopropiononitrile, N-(3-acetoxy-1-propyl)-N-(cyanomethyl)-aminoacetonitrile was synthesized.

Synthesis Example 37

Synthesis of N-cyanomethyl-N-(3-formyloxy-1-propyl)amino-acetonitrile (Amine 37)

By following the same procedure as Synthesis Example 4 except that N-cyanomethyl-N-(3-hydroxy-1-propyl) aminoacetonitrile was used instead of N,N-bis(2-hydroxyethyl)-3-aminopropiononitrile, N-cyanomethyl-N-(3-formyloxy-1-propyl)-aminoacetonitrile was synthesized.

Synthesis Example 38

Synthesis of N,N-bis(cyanomethyl)aminoacetonitrile (Amine 38)

To a mixture of 28% aqueous ammonia and 50.0 g of triethylamine at 0° C. was added 19.8 g of bromoacetonitrile. The mixture was heated at 70° C. for 20 hours. The reaction solution was diluted with ethyl acetate and the resulting solids were filtered off. Vacuum concentration yielded N,N-bis(cyanomethyl)aminoacetonitrile.

Synthesis Example 39

Synthesis of 1-pyrrolidinepropiononitrile (Amine 39)

At 20 to 30° C., 5.31 g of acrylonitrile was added to 7.11 g of pyrrolidine, which was stirred for 2 hours. Purification by vacuum distillation yielded 1-pyrrolidine-propiononitrile.

Synthesis Example 40

Synthesis of 1-piperidinepropiononitrile (Amine 40)

By following the same procedure as Synthesis Example 39 except that piperidine was used instead of pyrrolidine, 1-piperidinepropiononitrile was synthesized l(boiling point: 110° C./210 Pa).

Synthesis Example 41

Synthesis of 4-morpholinepropiononitrile (Amine 41)

By following the same procedure as Synthesis Example 39 except that morpholine was used instead of pyrrolidine, 4-morpholinepropiononitrile was synthesized (boiling point: 97° C./120 Pa).

IR (thin film): ν=2956, 2856, 2818, 2249, 1458, 1448, 1360, 1292, 1275, 1144, 1117, 1009 cm$^{-1}$ $^{1}$H-NMR (300 MHz in CDCl$_3$): δ=2.40–2.55 (6H, m), 2.65 (2H, m), 3.68 (4H, m)

Synthesis Example 42

Synthesis of 1-pyrrolidineacetonitrile (Amine 42)

At 20 to 30° C., 6.00 g of bromoacetonitrile was added 7.11 g of pyrrolidine, which was stirred for 2 hours. The reaction solution was diluted with ethyl acetate, washed with water, and concentrated in vacuum, obtaining 1-pyrrolidineacetonitrile.

Synthesis Example 43

Synthesis of 1-piperidineacetonitrile (Amine 43)

By following the same procedure as Synthesis Example 42 except that piperidine was used instead of pyrrolidine, 1-piperidineacetonitrile was synthesized.

Synthesis Example 44

Synthesis of 4-morpholineacetonitrile (Amine 44)

By following the same procedure as Synthesis Example 42 except that morpholine was used instead of pyrrolidine, 4-morpholineacetonitrile was synthesized.

IR (thin film): ν=2980, 2937, 2866, 2829, 2231, 1462, 1427, 1321, 1294, 1144, 1111, 1072, 1009, 893, 852 cm$^{-1}$
$_1$H-NMR (300 MHz in CDCl$_3$): δ=2.57 (4H, m), 3.49 (2H, s), 3.72 (4H, m)

Synthesis Example 45

Synthesis of cyanomethyl 3-diethylaminopropionate (Amine 45)

At 20 to 30° C., 22.2 g of cyanomethyl acrylate was added to 14.6 g of diethylamine, which was stirred for 10 hours, obtaining cyanomethyl 3-diethylaminopropionate.

Synthesis Example 46

Synthesis of cyanomethyl N,N-bis(2-hydroxyethyl)-3-aminopropionate (Amine 46)

By following the same procedure as Synthesis Example 45 except that diethanolamine was used instead of diethylamine, cyanomethyl N,N-bis(2-hydroxyethyl)-3-aminopropionate was synthesized.

Synthesis Example 47

Synthesis of cyanomethyl N,N-bis(2-acetoxyethyl)-3-aminopropionate (Amine 47)

By following the same procedure as Synthesis Example 3 except that cyanomethyl N,N-bis(2-hydroxyethyl)-3-aminopropionate was used instead of N,N-bis(2-hydroxyethyl)-3-aminopropiononitrile, cyanomethyl N,N-bis(2-acetoxyethyl)-3-aminopropionate was synthesized.

Synthesis Example 48

Synthesis of cyanomethyl N,N-bis(2-formyloxyethyl)-3-aminopropionate (Amine 48)

By following the same procedure as Synthesis Example 4 except that cyanomethyl N,N-bis(2-hydroxyethyl)-3-aminopropionate was used instead of N,N-bis(2-hydroxyethyl)-3-aminopropiononitrile, cyanomethyl N,N-bis(2-formyloxyethyl)-3-aminopropionate was synthesized.

Synthesis Example 49

Synthesis of cyanomethyl N,N-bis(2-methoxyethyl)-3-aminopropionate (Amine 49)

By following the same procedure as Synthesis Example 45 except that bis(2-methoxyethyl)amine was used instead of diethylamine, cyanomethyl N,N-bis(2-methoxyethyl)-3-aminopropionate was synthesized.

Synthesis Example 50

Synthesis of cyanomethyl N,N-bis[2-(methoxymethoxy)ethyl]-3-aminopropionate (Amine 50)

By following the same procedure as Synthesis Example 45 except that bis[2-(methoxymethoxy)ethyl]amine was used instead of diethylamine, cyanomethyl N,N-bis[2-(methoxymethoxy)ethyl]-3-aminopropionate was synthesized.

Synthesis Example 51

Synthesis of 2-cyanoethyl 3-diethylaminopropionate (Amine 51)

By following the same procedure as Synthesis Example 45 except that cyanoethyl acrylate was used instead of cyanomethyl acrylate, 2-cyanoethyl 3-diethylaminopropionate was synthesized.

Synthesis Example 52

Synthesis of 2-cyanoethyl N,N-bis(2-hydroxyethyl)-3-aminopropionate (Amine 52)

By following the same procedure as Synthesis Example 51 except that diethanolamine was used instead of diethylamine, 2-cyanoethyl N,N-bis(2-hydroxyethyl)-3-aminopropionate was synthesized.

Synthesis Example 53

Synthesis of 2-cyanoethyl N,N-bis(2-acetoxyethyl)-3-aminopropionate (Amine 53)

By following the same procedure as Synthesis Example 3 except that 2-cyanoethyl N,N-bis(2-hydroxyethyl)-3-aminopropionate was used instead of N,N-bis(2-hydroxyethyl)-3-aminopropiononitrile, 2-cyanoethyl N,N-bis(2-acetoxyethyl)-3-aminopropionate was synthesized (yield 90%).

IR (thin film): ν=2966, 2837, 2252, 1736, 1456, 1371, 1238, 1188, 1041 cm$^{-1}$ $^1$H-NMR (300 MHz in CDCl$_3$): δ=2.04 (6H, s), 2.48 (2H, t, J=7.1 Hz), 2.70 (2H, t, J=6.2 Hz), 2.75 (4H, t, J=5.9 Hz), 2.88 (2H, t, J=7.1 Hz), 4.08 (4H, t, J=5.9 Hz), 4.26 (2H, t, J=6.2 Hz)

Synthesis Example 54

Synthesis of 2-cyanoethyl N,N-bis(2-formyloxyethyl)-3-aminopropionate (Amine 54)

By following the same procedure as Synthesis Example 4 except that 2-cyanoethyl N,N-bis(2-hydroxyethyl)-3-aminopropionate was used instead of N,N-bis(2-hydroxyethyl)-3-aminopropiononitrile, 2-cyanoethyl N,N-bis(2-formyloxy-ethyl)-3-aminopropionate was synthesized.

Synthesis Example 55

Synthesis of 2-cyanoethyl N,N-bis(2-methoxyethyl)-3-aminopropionate (Amine 55)

By following the same procedure as Synthesis Example 51 except that bis(2-methoxyethyl)amine was used instead of diethylamine, 2-cyanoethyl N,N-bis(2-methoxyethyl)-3-aminopropionate was synthesized (boiling point: 132° C./27 Pa, yield: 90%).

IR (thin film): ν=2929, 2877, 2819, 2252, 1740, 1458, 1332, 1246, 1182, 1119, 1055, 1012 cm$^{-1}$ $^1$H-NMR (300 MHz in CDCl$_3$): δ=2.51 (2H, t, J=7.2 Hz), 2.69 (2H, t, J=6.3 Hz), 2.70 (4H, t, J=5.9 Hz), 2.90 (2H, t, J=7.2 Hz), 3.31 (6H, s), 3.43 (4H, t, J 5.9 Hz), 4.26 (2H, t, J 6.3 Hz)

Synthesis Example 56

Synthesis of 2-cyanoethyl N,N-bis[2-(methoxymethoxy)ethyl]-3-aminopropionate (Amine 56)

By following the same procedure as Synthesis Example 51 except that bis[2-(methoxymethoxy)ethyl]amine was used instead of diethylamine, 2-cyanoethyl N,N-bis[2-(methoxymethoxy)ethyl]-3-aminopropionate was synthesized.

Synthesis Example 57

Synthesis of cyanomethyl 1-pyrrolidinepropionate (Amine 57)

By following the same procedure as Synthesis Example 45 except that pyrrolidine was used instead of diethylamine, cyanomethyl 1-pyrrolidinepropionate was synthesized.

Synthesis Example 58

Synthesis of cyanomethyl 1-piperidinepropionate (Amine 58)

By following the same procedure as Synthesis Example 45 except that piperidine was used instead of diethylamine, cyanomethyl 1-piperidinepropionate was synthesized.

Synthesis Example 59

Synthesis of cyanomethyl 4-morpholinepropionate (Amine 59)

By following the same procedure as Synthesis Example 45 except that morpholine was used instead of diethylamine, cyanomethyl 4-morpholinepropionate was synthesized.

Synthesis Example 60

Synthesis of 2-cyanoethyl 1-pyrrolidinepropionate (Amine 60)

By following the same procedure as Synthesis Example 51 except that pyrrolidine was used instead of diethylamine, 2-cyanoethyl 1-pyrrolidinepropionate was synthesized.

Synthesis Example 61

Synthesis of 2-cyanoethyl 1-piperidinepropionate (Amine 61)

By following the same procedure as Synthesis Example 51 except that piperidine was used instead of diethylamine, 2-cyanoethyl 1-piperidinepropionate was synthesized.

Synthesis Example 62

Synthesis of 2-cyanoethyl 4-morpholinepropionate (Amine 62)

By following the same procedure as Synthesis Example 51 except that morpholine was used instead of diethylamine, 2-cyanoethyl 4-morpholinepropionate was synthesized.

Synthesis Example 63

Synthesis of N-(2-cyanoethyl)-N-(2-hydroxypropyl)-3-aminopropiononitrile (Amine 63)

By following the same procedure as Synthesis Example 10 except that 2-amino-1-propanol was used instead of ethylamine, N-(2-cyanoethyl)-N-(2-hydroxypropyl)-3-aminopropiononitrile was synthesized.

Synthesis Example 64

Synthesis of N-(2-acetoxypropyl)-N-(2-cyanoethyl)-3-aminopropiononitrile (Amine 64)

By following the same procedure as Synthesis Example 3 except that N-(2-cyanoethyl)-N-(2-hydroxypropyl)-3-aminopropiononitrile was used instead of N,N-bis(2-hydroxyethyl)-3-aminopropiononitrile, N-(2-acetoxypropyl)-N-(2-cyanoethyl)-3-aminopropiononitrile was synthesized (boiling point: 160° C./20 Pa, yield: 86%).

IR (thin film): ν=2980, 2937, 2846, 2249, 1732, 1464, 1423, 1373, 1247, 1130, 1092, 1063, 1020, 960 cm$^{-1}$ 1H-NMR (270 MHz in CDCl$_3$): δ=1.22 (3H, d, J=6.2 Hz), 2.05 (3H, s), 2.47 (4H, m), 2.57 (1H, dd, J=13.9, 4.9 Hz), 2.65 (1H, dd, J=13.9, 7.0 Hz), 2.90 (4H, m), 4.97 (1H, ddq, J=6.2, 7.0, 4.9 Hz)

Synthesis Example 65

Synthesis of N-(2-cyanoethyl)-N-[2-(2-hydroxyethoxy)ethyl]-3-aminopropiononitrile (Amine 65)

By following the same procedure as Synthesis Example 10 except that 2-(2-aminoethoxy)ethanol was used instead of ethylamine, N-(2-cyanoethyl)-N-[2-(2-hydroxyethoxy)ethyl]-3-aminopropiononitrile was synthesized.

Synthesis Example 66

Synthesis of N-[2-(2-acetoxyethoxy)ethyl]-N-(2-cyanoethyl)-3-aminopropiononitrile (Amine 66)

By following the same procedure as Synthesis Example 3 except that N-(2-cyanoethyl)-N-[2-(2-hydroxyethoxy)ethyl]-3-aminopropiononitrile was used instead of N,N-bis(2-hydroxy-ethyl)-3-aminopropiononitrile, N-[2-(2-acetoxyethoxy)ethyl]-N-(2-cyanoethyl)-3-aminopropiononitrile was synthesized (boiling point: 194° C./20 Pa, yield: 91%).

IR (thin film): ν=2952, 2865, 2247, 1736, 1456, 1423, 1373, 1248, 1128, 1053 cm$^{-1}$ $^1$H-NMR (270 MHz in CDCl$_3$): δ=2.07 (3H, s), 2.49 (4H, t, J=6.8 Hz), 2.80 (2H, t, J=5.1 Hz), 2.95 (4H, t, J=6.8 Hz), 3.56 (2H, t, J=5.1 Hz), 3.63 (2H, m), 4.20 (2H, m)

Synthesis Example 67

Synthesis of 4-morpholinobutyronitrile (Amine 67)

A mixture of 10.0 g of 4-bromobutyronitrile, 14.7 g of morpholine and 40 g of tetrahydrofuran was heated under reflux for 10 hours. The reaction solution was cooled, diluted with diethyl ether, filtered, and concentrated in vacuum. Purification by vacuum distillation yielded 9.4 g of 4-morpholinobutyronitrile (boiling point: 85° C./50 Pa, yield: 91%).

IR (thin film): ν=2954, 2854, 2812, 2247, 1458, 1360, 1304, 1277, 1269, 1142, 1119, 1072, 1036, 1024, 1011, 966, 918, 866 cm$^{-1}$ $^1$H-NMR (300 MHz in CDCl$_3$): δ=1.79 (2H, tt, J=6.9, 6.9 Hz), 2.35–2.50 (8H, m), 3.67 (4H, m)

Synthesis Example 68

Synthesis of N-(2-cyanoethyl)-N-tetrahydrofurfuryl-3-aminopropiononitrile (Amine 68)

By following the same procedure as Synthesis Example 10 except that tetrahydrofurfurylamine was used instead of ethylamine, N-(2-cyanoethyl)-N-tetrahydrofurfuryl-3-aminopropiononitrile was synthesized (boiling point: 143° C./15 Pa, yield: 90%).

IR (thin film): ν=2953, 2866, 2247, 1464, 1421, 1367, 1277, 1142, 1065, 1034, 985, 920 cm$^{-1}$ $^1$H-NMR (270 MHz in CDCl$_3$): δ=1.50 (1H, m), 1.75–2.05 (3H, m), 2.49 (4H, t, J=6.8 Hz), 2.63 (1H, dd, J=14.3, 6.8 Hz), 2.71 (1H, dd, J=14.3, 4.6 Hz), 2.97 (4H, t, J=6.8 Hz), 3.65–4.00 (3H, m)

Synthesis Example 69

Synthesis of N-(2-cyanoethyl)-N-(2,2-dimethoxyethyl)-3-aminopropiononitrile (Amine 69)

By following the same procedure as Synthesis Example 10 except that 2,2-dimethoxyethylamine was used instead of ethylamine, N-(2-cyanoethyl)-N-(2,2-dimethoxyethyl)-3-aminopropiononitrile was synthesized (boiling point: 135° C./13 Pa, yield: 86%).

IR (thin film): ν=2939, 2835, 2247, 1466, 1446, 1423, 1367, 1340, 1192, 1126, 1076, 972 cm$^{-1}$ $^1$H-NMR (270 MHz in CDCl$_3$): δ=2.48 (4H, t, J=6.9 Hz), 2.71 (2H, d, J=5.0 Hz), 2.96 (4H, t, J=6.9 Hz), 3.39 (6H, s), 4.36 (1H, t, J=5.0 Hz)

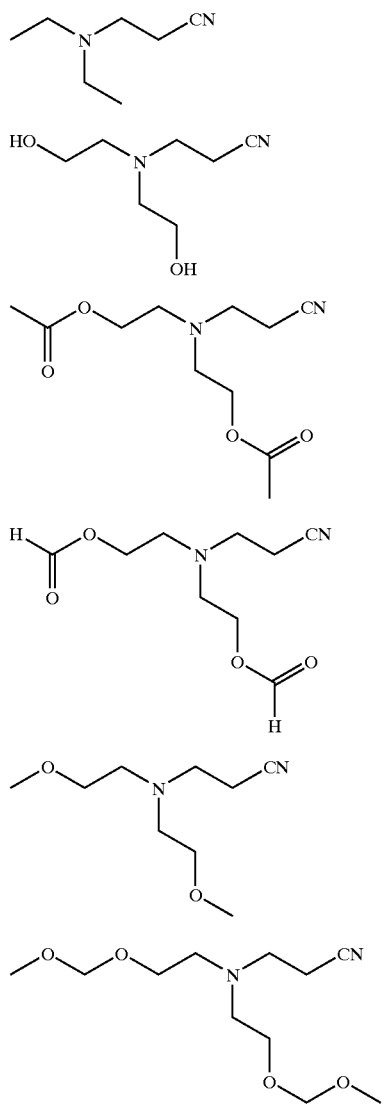

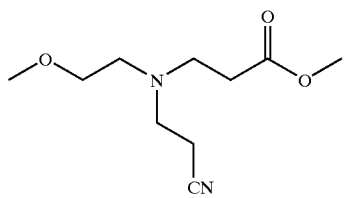

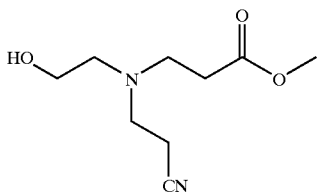

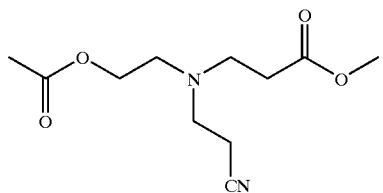

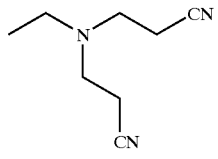

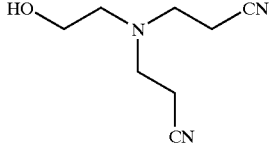

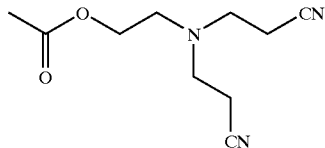

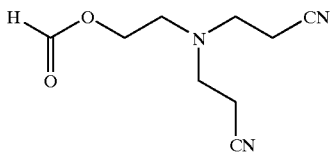

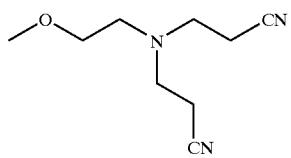

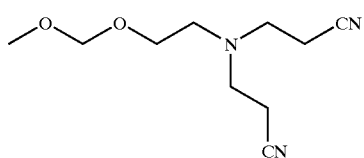

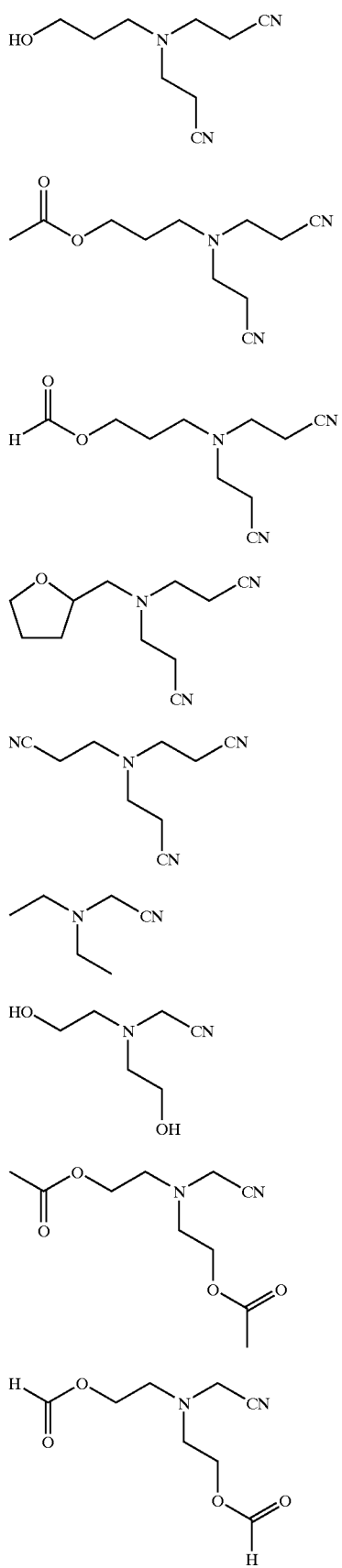
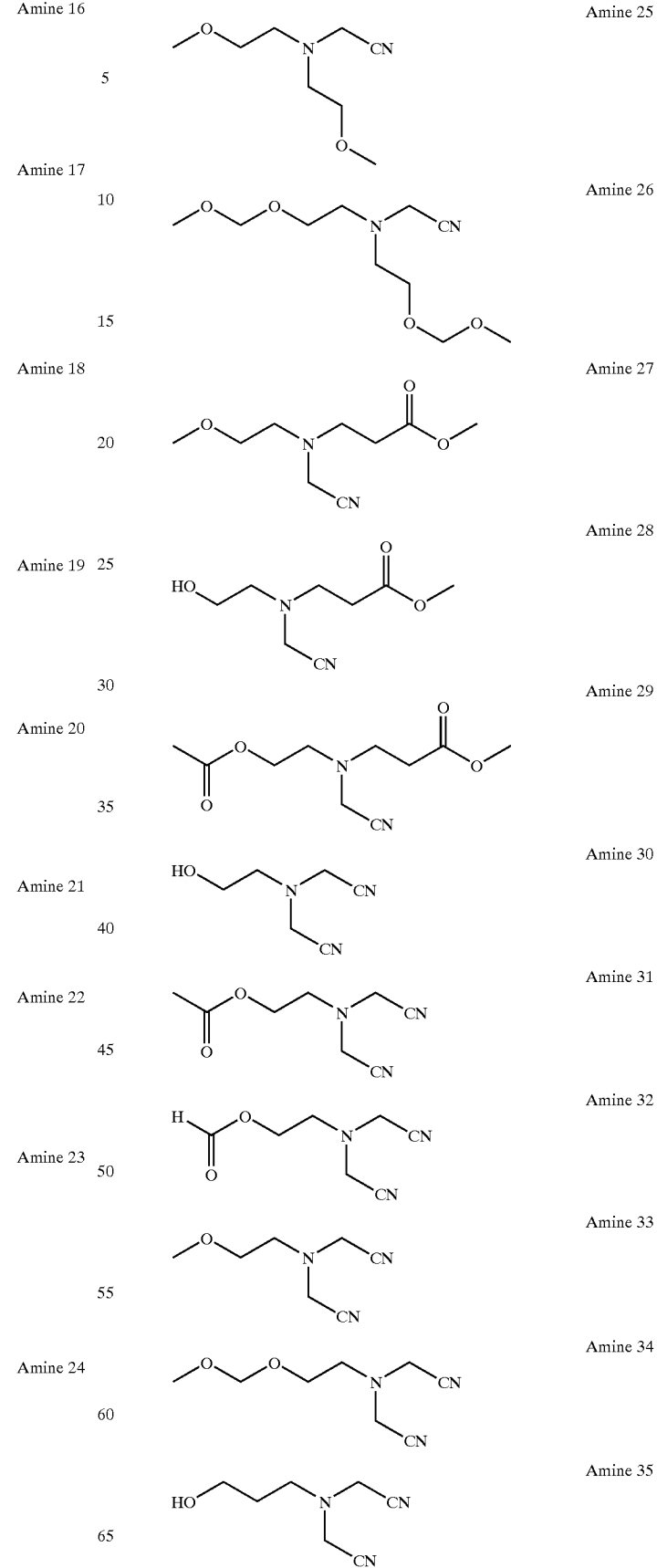

Amine 36
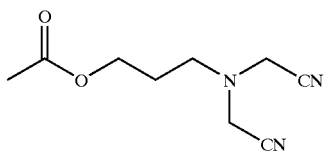
Amine 37
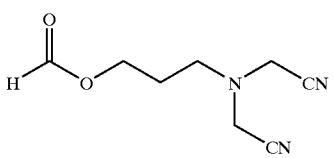
Amine 38
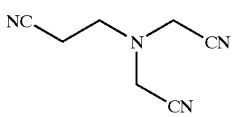
Amine 39
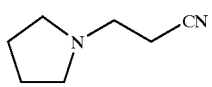
Amine 40
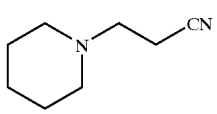
Amine 41
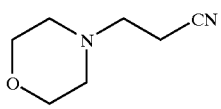
Amine 42
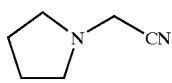
Amine 43
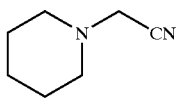
Amine 44
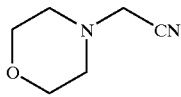
Amine 45
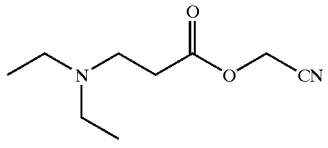
Amine 46
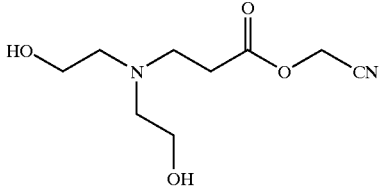
Amine 47
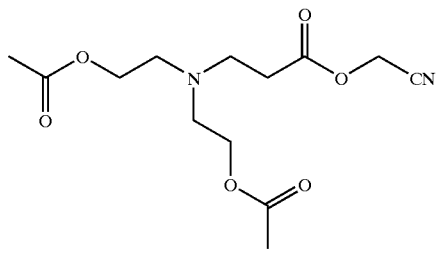
Amine 48
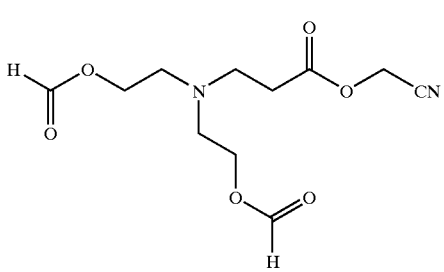
Amine 49
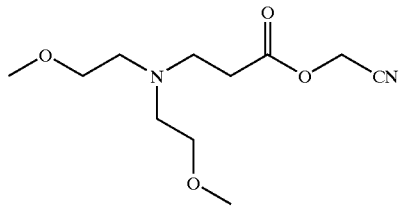
Amine 50
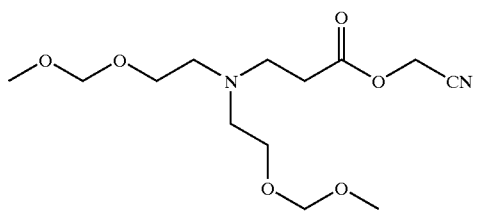
Amine 51
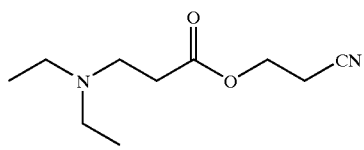
Amine 52
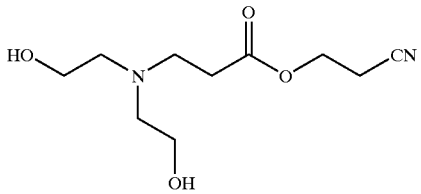
Amine 53
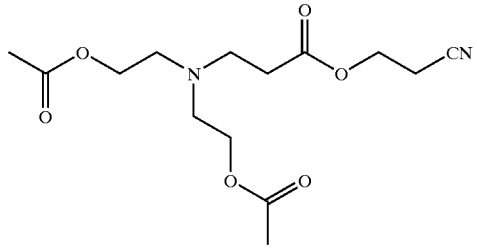

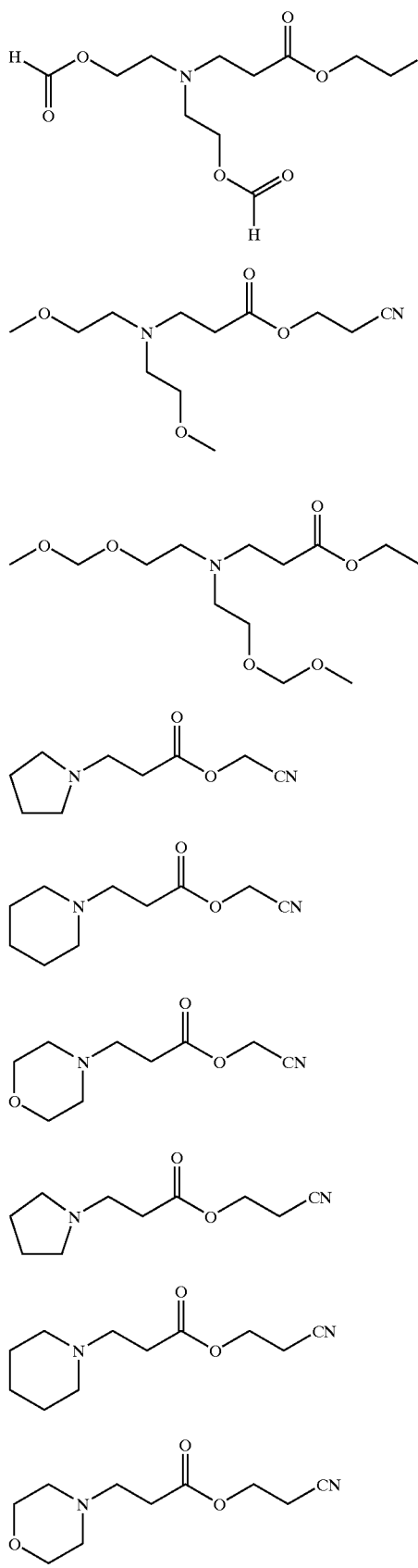

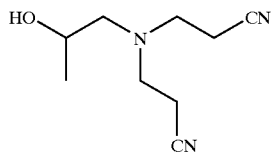

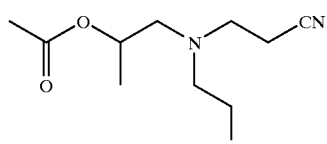

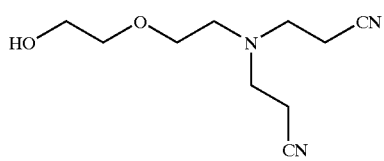

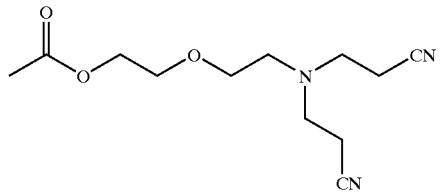

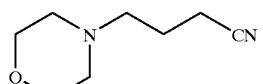

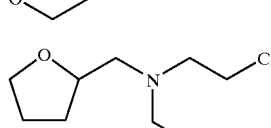

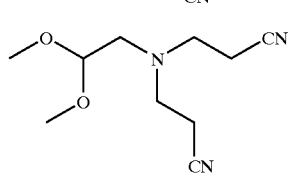

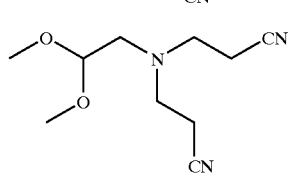

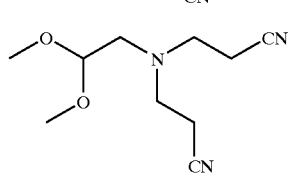

Examples and Comparative Examples

Resist solutions were prepared by dissolving the amine compound (Amines 1 through 62) synthesized above or another basic compound, polymer (Polymers 1 to 10 shown below), photoacid generator (PAG1 to 5), dissolution inhibitor (DRI) and crosslinker, all identified below, in a solvent mixture of propylene glycol monomethyl ether acetate (PGMEA) and ethyl lactate (EL) in a 70:30 ratio in the amounts shown in Tables and passing through a Teflon® filter having a pore size of 0.1 μm.

On silicon wafers, DUV-30 (Nissan Chemical Industries Ltd.) was coated to form films of 55 nm thick so that the reflectance to KrF light (248 nm) was reduced below 1%. On the coated substrates, the resist solutions were spin coated, then baked on a hot plate at 100° C. for 90 seconds to give resist films having a thickness of 550 nm.

The resist films were exposed by means of a KrF excimer laser stepper (NSR-S202A from Nikon Corporation; NA 0.6, σ0.75, ⅔ annular zone illumination) while the exposure dose and focus were varied. Immediately after exposure, the resist films were baked at 110° C. for 90 seconds and then developed for 60 seconds with a 2.38% aqueous solution of tetramethylammonium hydroxide, thereby giving patterns.

The resulting resist patterns were evaluated as described below. The exposure dose providing a 1:1 resolution at the top and bottom of a 0.16-μm line-and-space pattern was the optimum exposure dose (sensitivity Eop). A focus margin at the optimum exposure dose was determined. The definition of focus margin is that the pattern film experiences no thinning and the size falls within 0.16 μm±10%. The results are also shown in Tables 1 to 4 (Examples) and Table 5 (Comparative Examples).

Separately, resist compositions comprising phenol-free polymers were also evaluated by an exposure test to ArF excimer laser beam (193 nm). The resist solutions were prepared as above and spin coated on silicon wafers (on which DUV-30 (Nissan Chemical Industries Ltd.) had been coated to form films of 42 nm thick so that the reflectance to ArF light (193 nm) was reduced below 1%), then baked on a hot plate at 100° C. for 90 seconds to give resist films having a thickness of 350 nm.

The resist films were exposed by means of an ArF excimer laser stepper (Nikon Corporation; NA 0.55, σ0.8, ⅔ annular zone illumination) while the exposure dose and focus were varied. Immediately after exposure, the resist films were baked at 110° C. for 90 seconds and then developed for 60 seconds with a 2.38% aqueous solution of tetramethylammonium hydroxide, thereby giving patterns.

The resulting resist patterns were evaluated as described below. The exposure dose providing a 1:1 resolution at the top and bottom of a 0.14-μm line-and-space pattern was the optimum exposure dose (sensitivity Eop). A focus margin at the optimum exposure dose was determined. The definition of focus margin is that the pattern film experiences no thinning and the size falls within 0.14 μm±10%. The results are also shown in Table 6 (Examples) and Table 7 (Comparative Examples).

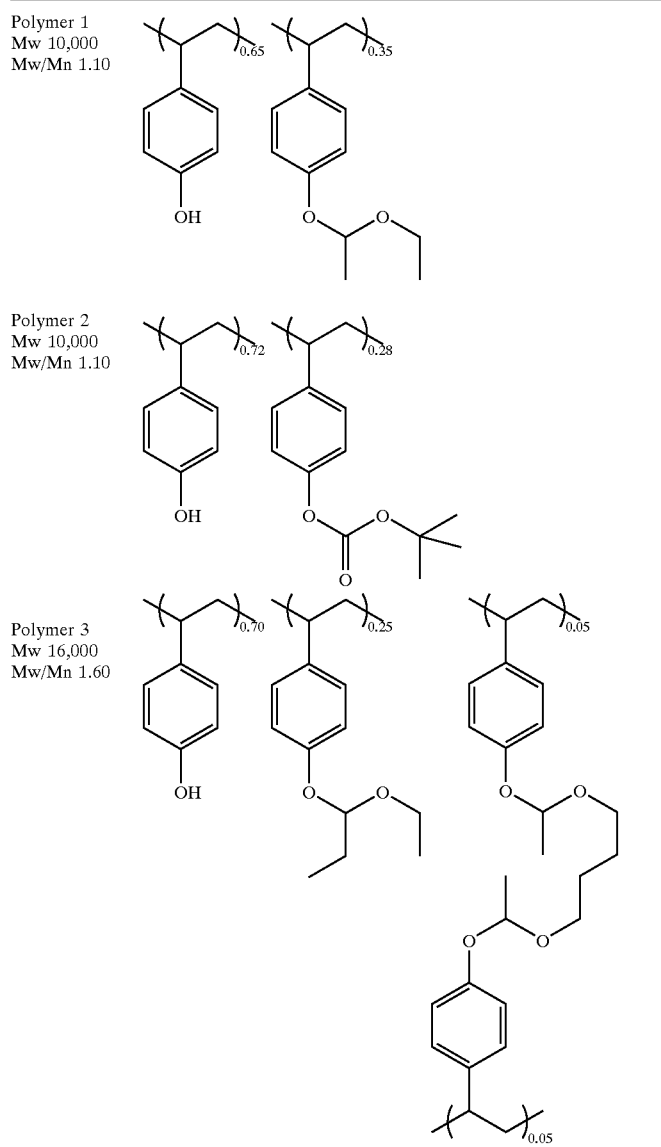

-continued
Polymer 4
Mw 10,000
Mw/Mn 1.10
Polymer 5
Mw 12,000
Mw/Mn 1.60
Polymer 6
Mw 10,000
Mw/Mn 1.60
Polymer 7
Mw 10,000
Mw/Mn 1.50
Polymer 8
Mw 11,000
Mw/Mn 1.58
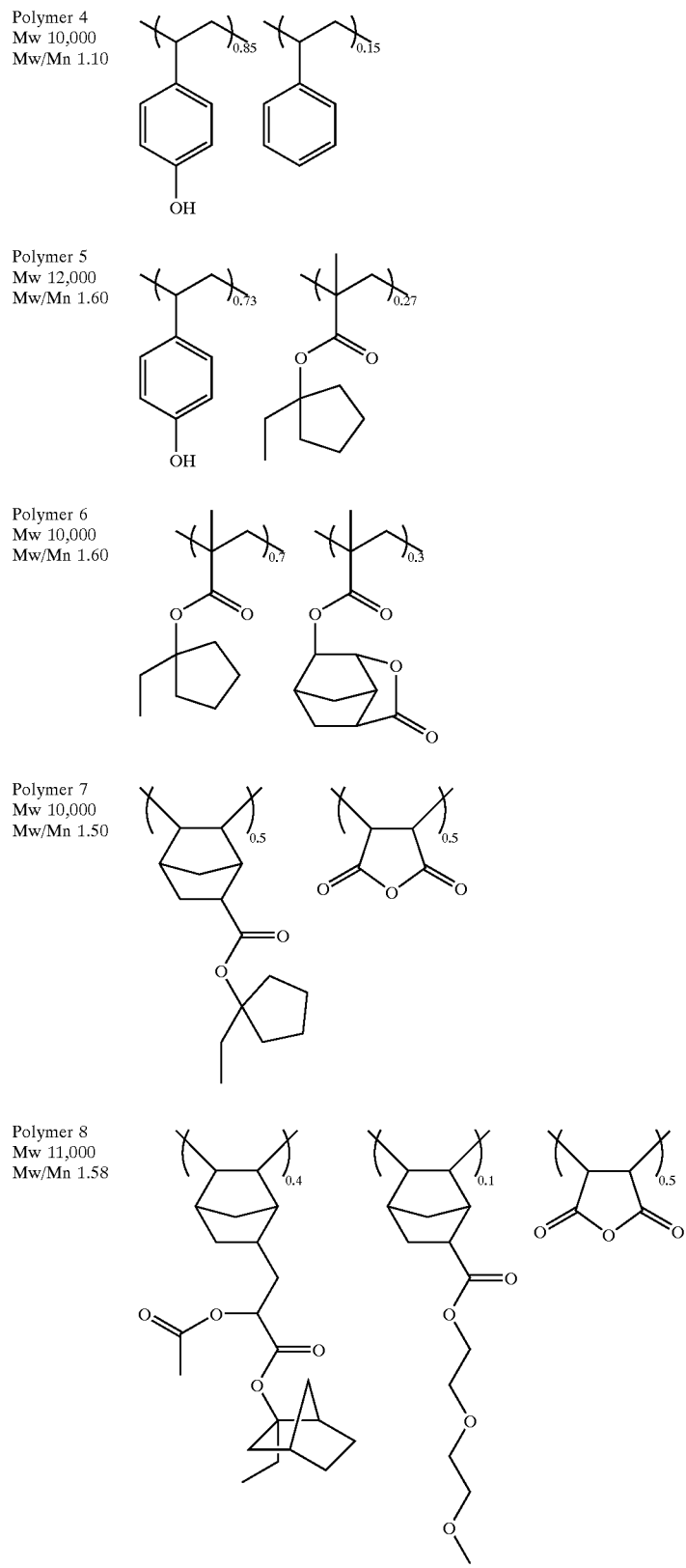

-continued
Polymer 9
Mw 18,000
Mw/Mn 2.0
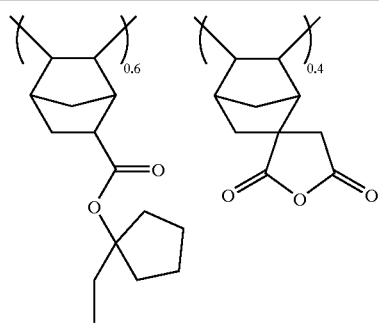
Polymer 10
Mw 13,000
Mw/Mn 1.20
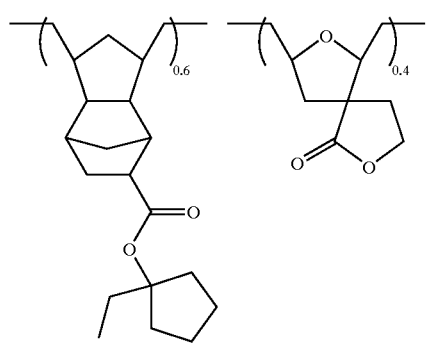
PAG 1
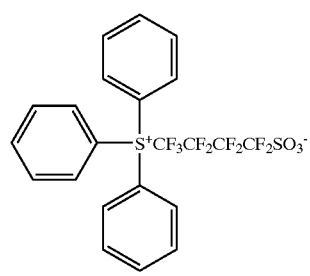
PAG 2
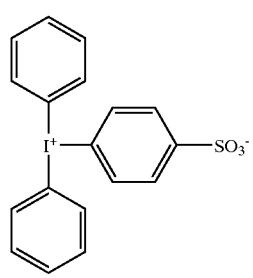
PAG 3
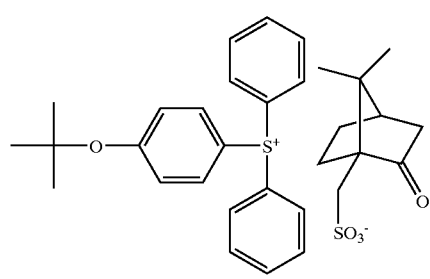
PAG 4
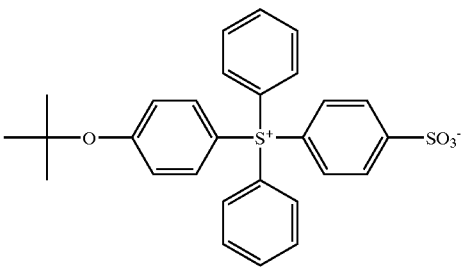
PAG 5
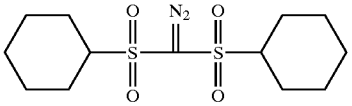
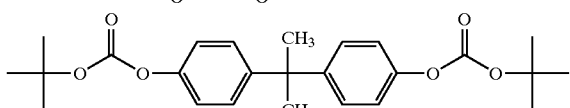
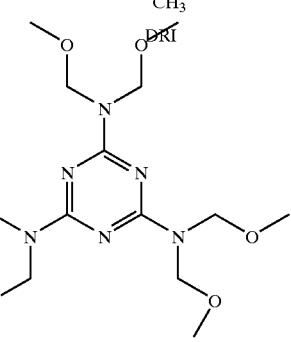
Crosslinker

TABLE 1

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 1 (100) | PAG 2 (2) | Amine 1 (0.1) | — | PGMEA/EL (600) | 30 | 0.8 |
| Polymer 1 (100) | PAG 2 (2) | Amine 2 (0.1) | — | PGMEA/EL (600) | 35 | 0.9 |
| Polymer 1 (100) | PAG 2 (2) | Amine 3 (0.1) | — | PGMEA/EL (600) | 31 | 1.0 |
| Polymer 1 (100) | PAG 2 (2) | Amine 4 (0.12) | — | PGMEA/EL (600) | 30 | 1.0 |
| Polymer 1 (100) | PAG 2 (2) | Amine 5 (0.12) | — | PGMEA/EL (600) | 33 | 1.0 |
| Polymer 1 (100) | PAG 2 (2) | Amine 6 (0.12) | — | PGMEA/EL (600) | 28 | 1.0 |
| Polymer 1 (100) | PAG 2 (2) | Amine 7 (0.12) | — | PGMEA/EL (600) | 32 | 1.0 |
| Polymer 1 (100) | PAG 2 (2) | Amine 8 (0.12) | — | PGMEA/EL (600) | 39 | 1.0 |
| Polymer 1 (100) | PAG 2 (2) | Amine 9 (0.12) | — | PGMEA/EL (600) | 38 | 1.0 |
| Polymer 1 (100) | PAG 2 (2) | Amine 10 (0.10) | — | PGMEA/EL (600) | 39 | 0.9 |
| Polymer 1 (100) | PAG 2 (2) | Amine 11 (0.10) | — | PGMEA/EL (600) | 40 | 1.0 |
| Polymer 1 (100) | PAG 2 (2) | Amine 12 (0.12) | — | PGMEA/EL (600) | 40 | 1.0 |
| Polymer 1 (100) | PAG 2 (2) | Amine 13 (0.12) | — | PGMEA/EL (600) | 39 | 1.0 |
| Polymer 1 (100) | PAG 2 (2) | Amine 14 (0.10) | — | PGMEA/EL (600) | 35 | 1.0 |
| Polymer 1 (100) | PAG 2 (2) | Amine 15 (0.11) | — | PGMEA/EL (600) | 36 | 1.0 |
| Polymer 1 (100) | PAG 2 (2) | Amine 16 (0.11) | — | PGMEA/EL (600) | 40 | 0.9 |
| Polymer 1 (100) | PAG 2 (2) | Amine 17 (0.12) | — | PGMEA/EL (600) | 38 | 1.0 |
| Polymer 1 (100) | PAG 2 (2) | Amine 18 (0.16) | — | PGMEA/EL (600) | 40 | 1.0 |
| Polymer 1 (100) | PAG 2 (2) | Amine 19 (0.10) | — | PGMEA/EL (600) | 36 | 0.9 |
| Polymer 1 (100) | PAG 2 (2) | Amine 20 (0.10) | — | PGMEA/EL (600) | 40 | 1.1 |

TABLE 2

| Polymer (pbw) | Photoacid generator (pbw) | Basic compound (pbw) | Dissolution inhibitor/ cross-linker (pbw) | Solvent (pbw) | Sensitivity (mJ/cm$^2$) | Focus margin ($\mu$m) |
|---|---|---|---|---|---|---|
| Polymer 1 (100) | PAG 2 (2) | Amine 21 (0.08) | — | PGMEA/EL (600) | 35 | 0.8 |
| Polymer 1 (100) | PAG 2 (2) | Amine 22 (0.10) | — | PGMEA/EL (600) | 36 | 0.9 |
| Polymer 1 (100) | PAG 2 (2) | Amine 23 (0.12) | — | PGMEA/EL (600) | 41 | 1.0 |
| Polymer 1 (100) | PAG 2 (2) | Amine 24 (0.11) | — | PGMEA/EL (600) | 40 | 1.0 |
| Polymer 1 (100) | PAG 2 (2) | Amine 25 (0.10) | — | PGMEA/EL (600) | 38 | 1.0 |
| Polymer 1 (100) | PAG 2 (2) | Amine 26 (0.12) | — | PGMEA/EL (600) | 37 | 1.0 |
| Polymer 1 (100) | PAG 2 (2) | Amine 27 (0.12) | — | PGMEA/EL (600) | 39 | 1.0 |
| Polymer 1 (100) | PAG 2 (2) | Amine 28 (0.11) | — | PGMEA/EL (600) | 34 | 1.0 |
| Polymer 1 (100) | PAG 2 (2) | Amine 29 (0.12) | — | PGMEA/EL (600) | 35 | 1.0 |
| Polymer 1 (100) | PAG 2 (2) | Amine 30 (0.10) | — | PGMEA/EL (600) | 34 | 0.9 |
| Polymer 1 (100) | PAG 2 (2) | Amine 31 (0.11) | — | PGMEA/EL (600) | 35 | 1.0 |

TABLE 2-continued

| Polymer (pbw) | Photoacid generator (pbw) | Basic compound (pbw) | Dissolution inhibitor/ cross-linker (pbw) | Solvent (pbw) | Sensitivity (mJ/cm$^2$) | Focus margin ($\mu$m) |
|---|---|---|---|---|---|---|
| Polymer 1 (100) | PAG 2 (2) | Amine 32 (0.16) | — | PGMEA/EL (600) | 40 | 1.0 |
| Polymer 1 (100) | PAG 2 (2) | Amine 33 (0.10) | — | PGMEA/EL (600) | 34 | 1.0 |
| Polymer 1 (100) | PAG 2 (2) | Amine 34 (0.12) | — | PGMEA/EL (600) | 34 | 1.0 |
| Polymer 1 (100) | PAG 2 (2) | Amine 35 (0.11) | — | PGMEA/EL (600) | 40 | 0.9 |
| Polymer 1 (100) | PAG 2 (2) | Amine 36 (0.12) | — | PGMEA/EL (600) | 41 | 1.0 |
| Polymer 1 (100) | PAG 2 (2) | Amine 37 (0.12) | — | PGMEA/EL (600) | 40 | 1.0 |
| Polymer 1 (100) | PAG 2 (2) | Amine 38 (0.12) | — | PGMEA/EL (600) | 42 | 1.0 |
| Polymer 1 (100) | PAG 2 (2) | Amine 39 (0.08) | — | PGMEA/EL (600) | 35 | 0.8 |
| Polymer 1 (100) | PAG 2 (2) | Amine 40 (0.08) | — | PGMEA/EL (600) | 34 | 0.8 |

TABLE 3

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 1 (100) | PAG 2 (2) | Amine 41 (0.09) | — | PGMEA/EL (600) | 35 | 0.8 |
| Polymer 1 (100) | PAG 2 (2) | Amine 42 (0.08) | — | PGMEA/EL (600) | 37 | 0.8 |
| Polymer 1 (100) | PAG 2 (2) | Amine 43 (0.08) | — | PGMEA/EL (600) | 35 | 0.8 |
| Polymer 1 (100) | PAG 2 (2) | Amine 44 (0.09) | — | PGMEA/EL (600) | 36 | 0.8 |
| Polymer 1 (100) | PAG 2 (2) | Amine 45 (0.12) | — | PGMEA/EL (600) | 36 | 0.8 |
| Polymer 1 (100) | PAG 2 (2) | Amine 46 (0.12) | — | PGMEA/EL (600) | 38 | 0.9 |
| Polymer 1 (100) | PAG 2 (2) | Amine 47 (0.14) | — | PGMEA/EL (600) | 36 | 1.0 |
| Polymer 1 (100) | PAG 2 (2) | Amine 48 (0.14) | — | PGMEA/EL (600) | 40 | 1.0 |
| Polymer 1 (100) | PAG 2 (2) | Amine 49 (0.14) | — | PGMEA/EL (600) | 40 | 1.0 |
| Polymer 1 (100) | PAG 2 (2) | Amine 50 (0.15) | — | PGMEA/EL (600) | 41 | 1.0 |
| Polymer 1 (100) | PAG 2 (2) | Amine 51 (0.12) | — | PGMEA/EL (600) | 35 | 0.8 |
| Polymer 1 (100) | PAG 2 (2) | Amine 52 (0.12) | — | PGMEA/EL (600) | 34 | 0.9 |
| Polymer 1 (100) | PAG 2 (2) | Amine 53 (0.14) | — | PGMEA/EL (600) | 41 | 1.0 |
| Polymer 1 (100) | PAG 2 (2) | Amine 54 (0.14) | — | PGMEA/EL (600) | 41 | 1.0 |
| Polymer 1 (100) | PAG 2 (2) | Amine 55 (0.14) | — | PGMEA/EL (600) | 41 | 1.0 |
| Polymer 1 (100) | PAG 2 (2) | Amine 56 (0.16) | — | PGMEA/EL (600) | 37 | 1.0 |
| Polymer 1 (100) | PAG 2 (2) | Amine 57 (0.10) | — | PGMEA/EL (600) | 41 | 0.8 |
| Polymer 1 (100) | PAG 2 (2) | Amine 58 (0.10) | — | PGMEA/EL (600) | 40 | 0.8 |
| Polymer 1 (100) | PAG 2 (2) | Amine 59 (0.10) | — | PGMEA/EL (600) | 39 | 0.8 |
| Polymer 1 (100) | PAG 2 (2) | Amine 60 (0.10) | — | PGMEA/EL (600) | 40 | 0.8 |

TABLE 4

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 1 (100) | PAG 2 (2) | Amine 61 (0.16) | — | PGMEA/EL (600) | 41 | 0.8 |
| Polymer 1 (100) | PAG 2 (2) | Amine 62 (0.10) | — | PGMEA/EL (600) | 39 | 0.8 |
| Polymer 2 (100) | PAG 2 (2) | Amine 3 (0.1) | — | PGMEA/EL (600) | 35 | 0.6 |
| Polymer 3 (100) | PAG 2 (2) | Amine 3 (0.1) | — | PGMEA/EL (600) | 31 | 1.1 |
| Polymer 4 (100) | PAG 2 (2) | Amine 3 (0.1) | Crosslinker (15) | PGMEA/EL (600) | 38 | 0.8 |
| Polymer 5 (100) | PAG 1 (2) | Amine 3 (0.1) | — | PGMEA/EL (600) | 33 | 0.8 |
| Polymer 6 (100) | PAG 1 (2) | Amine 3 (0.1) | — | PGMEA/EL (600) | 46 | 1.0 |
| Polymer 7 (100) | PAG 1 (2) | Amine 3 (0.1) | — | PGMEA/EL (600) | 48 | 1.0 |
| Polymer 8 (100) | PAG 1 (2) | Amine 3 (0.1) | — | PGMEA/EL (600) | 42 | 1.0 |
| Polymer 2 (100) | PAG 2 (2) | Amine 3 (0.1) | DRI (20) | PGMEA/EL (600) | 31 | 0.8 |
| Polymer 1 (100) | PAG 4 (2) | Amine 3 (0.1) | — | PGMEA/EL (600) | 45 | 1.0 |
| Polymer 1 (100) | PAG 5 (3) | Amine 3 (0.1) | — | PGMEA/EL (600) | 50 | 1.1 |
| Polymer 1 (100) | PAG 4 (1) PAG 5 (2) | Amine 3 (0.1) | — | PGMEA/EL (600) | 42 | 1.1 |

TABLE 5

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 1 (100) | PAG 2 (2) | — | — | PGMEA/EL (600) | 5 | 0 |
| Polymer 1 (100) | PAG 2 (2) | proton sponge (0.2) | — | PGMEA/EL (600) | 30 | 0.4 |
| Polymer 1 (100) | PAG 2 (2) | DBN (0.1) | — | PGMEA/EL (600) | 25 | 0.4 |
| Polymer 1 (100) | PAG 2 (2) | DBU (0.1) | — | PGMEA/EL (600) | 28 | 0.5 |
| Polymer 2 (100) | PAG 2 (2) | DBN (0.1) | — | PGMEA/EL (600) | 35 | 0.2 |
| Polymer 3 (100) | PAG 2 (2) | DBN (0.1) | — | PGMEA/EL (600) | 31 | 0.5 |
| Polymer 4 (100) | PAG 2 (2) | DBN (0.1) | Crosslinker (15) | PGMEA/EL (600) | 38 | 0.3 |
| Polymer 5 (100) | PAG 1 (2) | DBN (0.1) | — | PGMEA/EL (600) | 33 | 0.3 |
| Polymer 6 (100) | PAG 1 (2) | DBN (0.1) | — | PGMEA/EL (600) | 46 | 0.6 |
| Polymer 7 (100) | PAG 1 (2) | DBN (0.1) | — | PGMEA/EL (600) | 48 | 0.6 |
| Polymer 8 (100) | PAG 1 (2) | DBN (0.1) | — | PGMEA/EL (600) | 42 | 0.6 |
| Polymer 2 (100) | PAG 2 (2) | DBN (0.1) | DRI (20) | PGMEA/EL (600) | 31 | 0.4 |

TABLE 6

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 6 (100) | PAG 1 (2) | Amine 3 (0.1) | — | PGMEA/EL (600) | 12 | 0.6 |
| Polymer 6 (100) | PAG 1 (2) | Amine 12 (0.1) | — | PGMEA/EL (600) | 15 | 0.6 |
| Polymer 6 (100) | PAG 1 (2) | Amine 14 (0.1) | — | PGMEA/EL (600) | 17 | 0.6 |
| Polymer 6 (100) | PAG 1 (2) | Amine 21 (0.1) | — | PGMEA/EL (600) | 20 | 0.5 |
| Polymer 6 (100) | PAG 1 (2) | Amine 23 (0.1) | — | PGMEA/EL (600) | 13 | 0.6 |
| Polymer 6 (100) | PAG 1 (2) | Amine 41 (0.1) | — | PGMEA/EL (600) | 18 | 0.5 |
| Polymer 6 (100) | PAG 1 (2) | Amine 44 (0.1) | — | PGMEA/EL (600) | 19 | 0.5 |
| Polymer 7 (100) | PAG 1 (2) | Amine 3 (0.1) | — | PGMEA/EL (600) | 18 | 0.5 |
| Polymer 8 (100) | PAG 1 (2) | Amine 3 (0.1) | — | PGMEA/EL (600) | 15 | 0.6 |
| Polymer 9 (100) | PAG 1 (2) | Amine 3 (0.1) | — | PGMEA/EL (600) | 16 | 0.5 |
| Polymer 10 (100) | PAG 1 (2) | Amine 3 (0.1) | — | PGMEA/EL (600) | 20 | 0.4 |

TABLE 7

| Polymer (pbw) | Photoacid generator (pbw) | Basic compound (pbw) | Dissolution inhibitor/ crosslinker (pbw) | Solvent (pbw) | Sensitivity (mJ/cm$^2$) | Focus margin ($\mu$m) |
|---|---|---|---|---|---|---|
| Polymer 6 (100) | PAG 1 (2) | — | — | PGMEA/EL (600) | 3 | 0.2 |
| Polymer 6 (100) | PAG 1 (2) | proton sponge (0.2) | — | PGMEA/EL (600) | 18 | 0.1 |
| Polymer 6 (100) | PAG 1 (2) | DBN (0.1) | — | PGMEA/EL (600) | 11 | 0.2 |
| Polymer 6 (100) | PAG 1 (2) | DBU (0.1) | — | PGMEA/EL (600) | 10 | 0.2 |
| Polymer 7 (100) | PAG 1 (2) | proton sponge (0.2) | — | PGMEA/EL (600) | 20 | 0.1 |
| Polymer 8 (100) | PAG 1 (2) | proton sponge (0.2) | — | PGMEA/EL (600) | 17 | 0.2 |
| Polymer 9 (100) | PAG 1 (2) | proton sponge (0.2) | — | PGMEA/EL (600) | 13 | 0.1 |
| Polymer 10 (100) | PAG 1 (2) | proton sponge (0.2) | — | PGMEA/EL (600) | 25 | 0.1 |

Japanese Patent Application No. 2000-3,73316 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A resist composition comprising a basic compound having a cyano group, said basic compound selected from amine compounds of formulae (1), (2), (3) and (4):

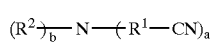 (1)

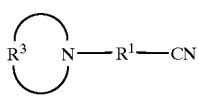 (2)

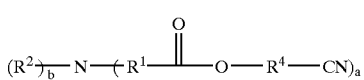 (3)

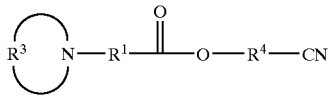 (4)

wherein R$^1$ is independently a straight or branched alkylene group of 1 to 4 carbon atoms, R$^2$ is independently hydrogen or a straight, branched or cyclic alkyl group of 1 to 20 carbon atoms which may contain a hydroxy group, ether group, carbonyl group, ester group, lactone ring, carbonate or cyano group, R³ is a straight or branched alkylene group of 2 to 20 carbon atoms which may contain a hydroxy group, ether group, thioether group, carbonyl group, ester group, thioester group or carbonate, R⁴ is independently a straight or branched alkylene group of 1 to 4 carbon atoms, "a" is an integer of 1 to 3, and a+b=3.

2. The resist composition of claim 1 wherein R² in formulae (1) and (3) has the following general formula (5), (6), (7) or (8):

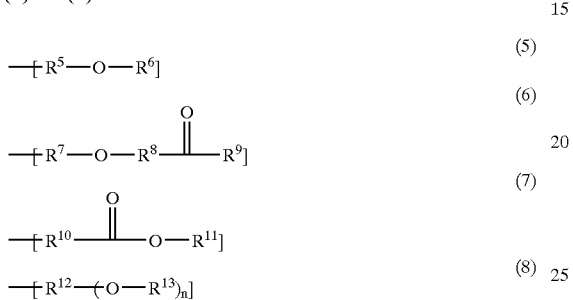

wherein R⁵, R⁷ and R¹⁰ each are a straight or branched alkylene group of 1 to 4 carbon atoms, R⁶ and R⁹ each are hydrogen or a straight, branched or cyclic alkyl group of 1 to 20 carbon atoms which may contain a hydroxy group, ether group, ester group, lactone ring or cyano group, R⁵ and R⁶, taken together, may form a ring with the oxygen atom, R⁸ is a single bond or a straight or branched alkylene group of 1 to 4 carbon atoms, R¹¹ is a straight, branched or cyclic alkyl group of 1 to 20 carbon atoms which may contain a hydroxy group, ether group, ester group or lactone ring, R¹² is a (n+1)-valent straight or branched organic group of 1 to 4 carbon atoms, R¹³ is independently a straight, branched or cyclic alkyl group of 1 to 10 carbon atoms which may contain an ether group, ester group, hydroxy group, lactone ring, cyano group or carbonyl group, R¹² and R¹³ or two R¹³ groups, taken together, may form a ring with the oxygen atom or the oxygen atom and a carbon atom in R¹², and n is equal to 2, 3 or 4.

3. A resist composition according to claim 2, further comprising (B) an organic solvent, (C) a base resin, and (D) a photoacid generator.

4. A resist composition according to claim 3, wherein R¹² is selected from

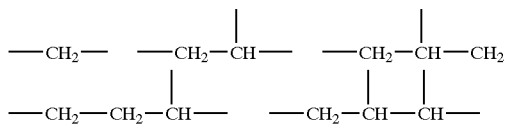

5. A resist composition according to claim 1, further comprising (B) an organic solvent, (C) a base resin, and (D) a photoacid generator.

6. A resist composition according to claim 5, wherein R¹ and R⁴ are methylene, ethylene, propylene, or butylene.

7. A resist composition according to claim 5, wherein R² is hydrogen, methyl, ethyl, propyl, isopropyl, n-butyl, isobutyl, tert-butyl, pentyl, cyclopentyl, hexyl, cyclohexyl, octyl, decyl or dodecyl, which may contain a hydroxy group, ether group, carbonyl group, ester group, lactone ring, carbonate or cyano group.

8. A resist composition according to claim 5, wherein wherein moiety (A)

$$\underset{R^3}{\overset{}{\bigcap}} N- \quad \text{is} \tag{A}$$

$$\triangleright N{\dashv} \tag{A-1}$$

-continued

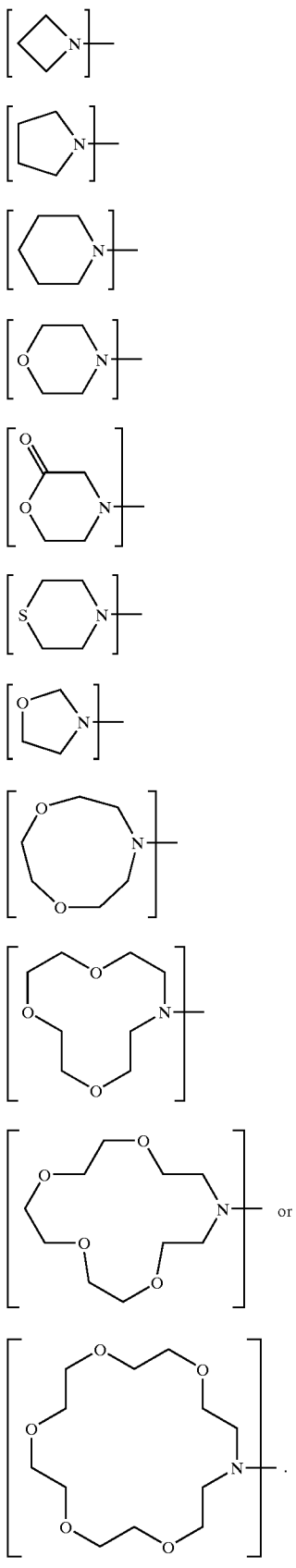

(A)-2
(A)-3
(A)-4
(A)-5
(A)-6
(A)-7
(A)-8
(A)-9
(A)-10
(A)-11
(A)-12

9. A resist composition according to claim 5, wherein the basic compound is selected from
(3-diethylamino)propiononitrile,
N,N-bis(2-hydroxyethyl)-3-aminopropiononitrile,
N,N-bis(2-acetoxyethyl)-3-aminopropiononitrile,
N,N-bis(2-formyloxyethyl)-3-aminopropiononitrile,
N,N-bis(2-methoxyethyl)-3-aminopropiononitrile,
N,N-bis[2-(methoxymethoxy)ethyl]-3-aminopropiononitrile,
methyl N-(2-cyanoethyl)-N-(2-methoxyethyl)-3-aminopropionate,
methyl N-(2-cyanoethyl)-N-(2-hydroxyethyl)-3-aminopropionate,
methyl N-(2-acetoxyethyl)-N-(2-cyanoethyl)-3-aminopropionate,
N-(2-cyanoethyl)-N-ethyl-3-aminopropiononitrile,
N-(2-cyanoethyl)-N-(2-hydroxyethyl)-3-aminopropiononitrile,
N-(2-acetoxyethyl)-N-(2-cyanoethyl)-3-aminopripiononitrile,
N-(2-cyanoethyl)-N-(2-formyloxyethyl)-3-aminopropiononitrile,
N-(2-cyanoethyl)-N-(2-methoxyethyl)-3-aminopropiononitrile,
N-(2-cyanoethyl)-N-[2-(methoxymethoxy)ethyl]-3-aminopropiononitrile,
N-(2-cyanoethyl)-N-(3-hydroxy-1-propyl)-3-aminopropiononitrile,
N-(3-acetoxy-1-propyl)-N-(2-cyanoethyl)-3-aminopropiononitrile,
N-(2-cyanoethyl)-N-(3-formyloxy-1-propyl)-3-aminopropiononitrile,
N-(2-cyanoethyl)-N-tetrahydrofurfuryl-3-aminopropiononitrile,
N,N-bis(2-cyanoethyl)-3-aminopropiononitrile,
diethylaminoacetonitrile,
N,N-bis(2-hydroxyethyl)aminoacetonitrile,
N,N-bis(2-acetoxyethyl)aminoacetonitrile,
N,N-bis(2-formyloxyethyl)aminoacetonitrile,
N,N-bis(2-methoxyethyl)aminoacetonitrile,
N,N-bis[2-(methoxymethoxy)ethyl]aminoacetonitrile,
methyl N-cyanomethyl-N-(2-methoxyethyl)-3-aminopropionate,
methyl N-cyanomethyl-N-(2-hydroxyethyl)-3-aminopropionate,
methyl N-(2-acetoxyethyl)-N-cyanomethyl-3-aminopropionate,
methyl N-cyanomethyl-N-(2-formyloxyethyl)aminopropionate,
N-cyanomethyl-N-(2-hydroxyethyl)aminoacetonitrile,
N-(2-acetoxyethyl)-N-(cyanomethyl)aminoacetonitrile,
N-cyanomethyl-N-(2-formyloxyethyl)aminoacetonitrile,
N-cyanomethyl-N-(2-methoxyethyl)aminoacetonitrile,
N-cyanomethyl-N-[2-(methoxymethoxy)ethyl]aminoacetonitrile,
N-(cyanomethyl)-N-(3-hydroxy-1-propyl)aminoacetonitrile,
N-(3-acetoxy-1-propyl)-N-(cyanomethyl)aminoacetonitrile,
N-cyanomethyl-N-(3-formyloxy-1-propyl)aminoacetonitrile, and N,N-bis(cyanomethyl)aminoacetonitrile.

10. A resist composition according to claim 5, wherein the basic compound is selected from 1-pyrrolidinepropiononitrile,
1-piperidinepropiononitrile,
4-morpholinepropiononitrile,
1-aziridinepropiononitrile,
1-azetidinepropiononitrile,
1-pyrrolidineacetonitrile,
1-piperidineacetonitrile, and
4-morpholineacetonitrile.

11. A resist composition according to claim 5, wherein the basic compound is selected from cyanomethyl 3-diethylaminopropionate,
cyanomethyl N,N-bis(2-hydroxyethyl)-3-aminopropionate,
cyanomethyl N,N-bis(2-acetoxyethyl)-3-aminopropionate,
cyanomethyl N,N-bis(2-formyloxyethyl)-3-aminopropionate,
cyanomethyl N,N-bis(2-methoxyethyl)-3-aminopropionate,
cyanomethyl N,N-bis[2-(methoxymethoxy)ethyl]-3-aminopropionate,
2-cyanoethyl 3-diethylaminopropionate,
2-cyanoethyl N,N-bis(2-hydroxyethyl)-3-aminopropionate,
2-cyanoethyl N,N-bis(2-acetoxyethyl)-3-aminopropionate,
2-cyanoethyl N,N-bis(2-formyloxyethyl)-3-aminopropionate,
2-cyanoethyl N,N-bis(2-methoxyethyl)-3-aminopropionate,
2-cyanoethyl N,N-bis[2-(methoxymethoxy)ethyl]-3-aminopropionate,
cyanomethyl N,N-bis(2-cyanoethyl)-3-aminopropionate,
2-cyanoethyl N,N-bis(2-cyanoethyl)-3-aminopropionate,
cyanomethyl N,N-bis(cyanomethyl)-3-aminopropionate, and
2-cyanoethyl N,N-bis(cyanomethyl)-3-aminopropionate.

12. A resist composition according to claim 5, wherein the basic compound is selected from cyanomethyl 1-pyrrolidinepropionate,
cyanomethyl 1-piperidinepropionate,
cyanomethyl 4-morpholinepropionate,
2-cyanoethyl 1-pyrrolidinepropionate,
2-cyanoethyl 1-piperidinepropionate, and
cyanomethyl 4-morpholinepropionate.

13. A positive resist composition comprising (A) an amine compound selected from compounds of formulae (1), (2), (3) and (4):

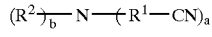 (1)

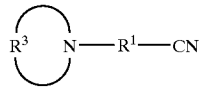 (2)

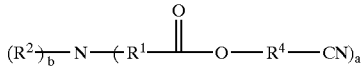 (3)

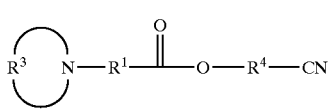 (4)

wherein $R^1$ is independently a straight or branched alkylene group of 1 to 4 carbon atoms, $R^2$ is independently hydrogen or a straight, branched or cyclic alkyl group of 1 to 20 carbon atoms which may contain a hydroxy group, ether group, carbonyl group, ester group, lactone ring, carbonate or cyano group, $R^3$ is a straight or branched alkylene group of 2 to 20 carbon atoms which may contain a hydroxy group, ether group, thioether group, carbonyl group, ester group, thioester group or carbonate, $R^4$ is independently a straight or branched alkylene group of 1 to 4 carbon atoms, "a" is an integer of 1 to 3, and a+b=3, (B) an organic solvent, (C) a base resin having an acidic functional group protected with an acid labile group, which is normally alkali insoluble or substantially alkali insoluble, but becomes alkali soluble upon elimination of the acid labile group, and (D) a photoacid generator.

14. The positive resist composition of claim 13 further comprising (E) a dissolution inhibitor.

15. A process for forming a resist pattern comprising the steps of:

applying the resist composition of claim 13 onto a substrate to form a coating, heat treating the coating and then exposing it to high-energy radiation having a wavelength of less than 300 nm or electron beams through a photo mask, and optionally heat treating the exposed coating and developing it with a developer.

16. A positive resist composition according to claim 13, wherein $R^2$ in formulae (1) and (3) has the following general formula (5), (6), (7) or (8):

 (5)

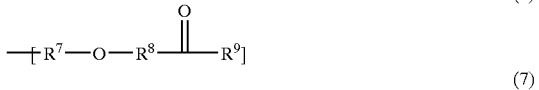 (6)

 (7)

 (8)

wherein $R^5$, $R^7$ and $R^{10}$ are, each independently, a straight or branched alkylene group of 1 to 4 carbon atoms; and $R^6$ and $R^9$ are, each independently, hydrogen or a straight, branched or cyclic alkyl group of 1 to 20 carbon atoms which optionally contains a hydroxy group, ether group, ester group, lactone ring or cyano group; or $R^5$ and $R^6$, taken together, optionally forms a ring with the oxygen atom;

$R^8$ is a single bond or a straight or branched alkylene group of 1 to 4 carbon atoms;

$R^{11}$ is a straight, branched or cyclic alkyl group of 1 to 20 carbon atoms that optionally contains a hydroxy group, ether group, ester group or lactone ring;

$R^{12}$ is a (n+1)-valent straight or branched organic group of 1 to 4 carbon atoms;

$R^{13}$ are, each independently, a straight, branched or cyclic alkyl group of 1 to 10 carbon atoms which optionally contains an ether group, ester group, hydroxy group, lactone ring, cyano group or carbonyl group, or $R^{12}$ and $R^{13}$, taken together, optionally bond with the oxygen atom to form a ring having 2 to 20 carbon atoms, and/or two $R^{13}$ groups, taken together, optionally bond with the oxygen atom or the oxygen atom and a carbon atom in $R^{12}$ to form a ring having 1 to 20 carbon atoms, and n is equal to 2, 3, or 4.

17. A negative resist composition comprising (A) an amine compound selected from compounds of formulae (1), (2), (3) and (4):

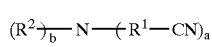  (1)

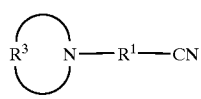  (2)

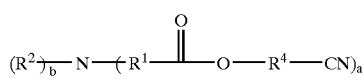  (3)

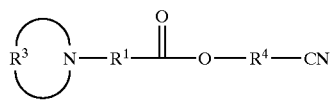  (4)

wherein $R^1$ is independently a straight or branched alkylene group of 1 to 4 carbon atoms, $R^2$ is independently hydrogen or a straight, branched or cyclic alkyl group of 1 to 20 carbon atoms which may contain a hydroxy group, ether group, carbonyl group, ester group, lactone ring, carbonate or cyano group, $R^3$ is a straight or branched alkylene group of 2 to 20 carbon atoms which may contain a hydroxy group, ether group, thioether group, carbonyl group, ester group, thioester group or carbonate, $R^4$ is independently a straight or branched alkylene group of 1 to 4 carbon atoms, "a" is an integer of 1 to 3, and a+b=3, (B) an organic solvent, (C) a base resin which is normally alkali soluble, but becomes substantially alkali insoluble when crosslinked with a crosslinker, (D) a photoacid generator, and (F) the crosslinker capable of crosslinking under the action of acid.

18. A negative resist composition according to claim 17, wherein $R^2$ in formulae (1) and (3) has the following general formula (5), (6), (7) or (8):

  (5)

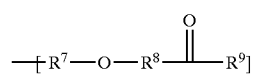  (6)

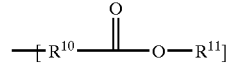  (7)

  (8)

wherein $R^5$, $R^7$ and $R^{10}$ are, each independently, a straight or branched alkylene group of 1 to 4 carbon atoms; and $R^6$ and $R^9$ are, each independently, hydrogen or a straight, branched or cyclic alkyl group of 1 to 20 carbon atoms which optionally contains a hydroxy group, ether group, ester group, lactone ring or cyano group; or $R^5$ and $R^6$, taken together, optionally forms a ring with the oxygen atom;

$R^8$ is a single bond or a straight or branched alkylene group of 1 to 4 carbon atoms;

$R^{11}$ is a straight, branched or cyclic alkyl group of 1 to 20 carbon atoms that optionally contains a hydroxy group, ether group, ester group or lactone ring;

$R^{12}$ is a (n+1)-valent straight or branched organic group of 1 to 4 carbon atoms;

$R^{13}$ are, each independently, a straight, branched or cyclic alkyl group of 1 to 10 carbon atoms which optionally contains an ether group, ester group, hydroxy group, lactone ring, cyano group or carbonyl group, or $R^{12}$ and $R^{13}$, taken together, optionally bond with the oxygen atom to form a ring having 2 to 20 carbon atoms, and/or two $R^{13}$ groups, taken together, optionally bond with the oxygen atom or the oxygen atom and a carbon atom in $R^{12}$ to form a ring having 1 to 20 carbon atoms, and n is equal to 2, 3, or 4.

19. An amine compound of the following general formula (1):

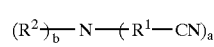  (1)

wherein $R^1$ is, each independently, a straight or branched alkylene group of 1 to 4 carbon atoms, a is an integer of 1 or 2, a+b is 3, and $R^2$ is a compound of formula (6)

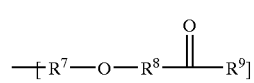  (6)

wherein $R^7$ is ethylene, $R^8$ is methylene, and $R^9$ is, each independently, a hydrogen or a straight, branched or cyclic alkyl group of 1 to 20 carbon atoms which optionally contains a hydroxy group, ether group, ester group, lactone ring or cyano group.

20. A positive resist composition comprising (A) a compound of formula (1) of claim 19, (B) an organic solvent, (C) a base resin having an acidic functional group protected with an acid labile group, which is normally alkali insoluble or substantially alkali insoluble, but becomes alkali soluble upon elimination of the acid labile group, and (D) a photoacid generator.

21. A positive resist composition according to claim 20, wherein $R^9$ is H, $CH_3$, $CH_2CH_3$, $CH_2C(O)OCH_3$, $CH_2OC(O)CH_3$, $CH_2OCH_3$, OCH, or $OC(CH_3)_3$.

22. A negative resist composition comprising (A) a compound of formula (1) of claim 19, (B) an organic solvent, (C) a base resin which is normally alkali soluble, but becomes substantially alkali insoluble when crosslinked with a crosslinker, (D) a photoacid generator, and (F) the crosslinker capable of crosslinking under the action of acid.

23. A negative resist composition according to claim 22, wherein $R^9$ is H, $CH_3$, $CH_2CH_3$, $CH_2C(O)OCH_3$, $CH_2OC(O)CH_3$, $CH_2OCH_3$, $OCH_3$, or $OC(CH_3)_3$.

24. An amine compound according to claim 19, wherein $R^9$ is H, $CH_3$, $CH_2CH_3$, $CH_2C(O)OCH_3$, $CH_2OC(O)CH_3$, $CH_2OCH_3$, $OCH_3$, or $OC(CH_3)_3$.

25. An amine compound of the following general formula (2):

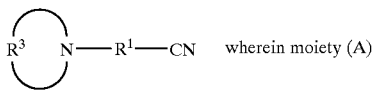   wherein moiety (A)   (2)

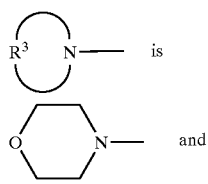

$R^1$ is a straight or branched alkylene group of 1 to 4 carbon atoms.

26. A positive resist composition comprising (A) a compound of formula (2) of claim 25, (B) an organic solvent, (C) a base resin having an acidic functional group protected with an acid labile group, which is normally alkali insoluble or substantially alkali insoluble, but becomes alkali soluble upon elimination of the acid labile group, and (D) a photoacid generator.

27. A negative resist composition comprising (A) a compound of formula (2) of claim 25, (B) an organic solvent, (C) a base resin which is normally alkali soluble, but becomes substantially alkali insoluble when crosslinked with a crosslinker, (D) a photoacid generator, and (F) the crosslinker capable of crosslinking under the action of acid.

* * * * *